(12) United States Patent
Corkey et al.

(10) Patent No.: US 6,300,055 B1
(45) Date of Patent: Oct. 9, 2001

(54) DIAGNOSTIC SCREENS FOR TYPE 1 DIABETES (IDDM)

(75) Inventors: Barbara E. Corkey; Nicholas R. Husni, both of Boston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/378,084

(22) Filed: Aug. 20, 1999

Related U.S. Application Data

(60) Provisional application No. 60/097,518, filed on Aug. 20, 1998.

(51) Int. Cl.[7] ............................. C12Q 1/00; G01N 33/53

(52) U.S. Cl. ............................................. 435/4; 435/975

(58) Field of Search .......................... 435/4, 975

(56) References Cited

U.S. PATENT DOCUMENTS 5,871,769 * 2/1999 Fleming et al. .................. 424/423

* cited by examiner

*Primary Examiner*—Louis N Leary
(74) *Attorney, Agent, or Firm*—Lahive & Cockfield, LLP; Giulio DeConti; Debra J. Milasincic

(57) ABSTRACT

The present invention features methods for diagnosing insulin-dependent diabetes mellitus (IDDM) in a test subject, for example a subject at risk of developing IDDM, which involve detecting hyper-responsive $Ca^{2+}$ mobilization in cells obtained from the test subject. Hyper-responsive $Ca^{2+}$ mobilization can be detected in cells contacted with a stimulatory agent, preferably in cells contacted with a potentiating agent and a stimulatory agent. Methods of the present invention include comparing $Ca^{2+}$ mobilization in cells from the test subject to $Ca^{2+}$ mobilization in cells from a control subject. The present invention further features kits for use in the detection of IDDM.

20 Claims, 16 Drawing Sheets

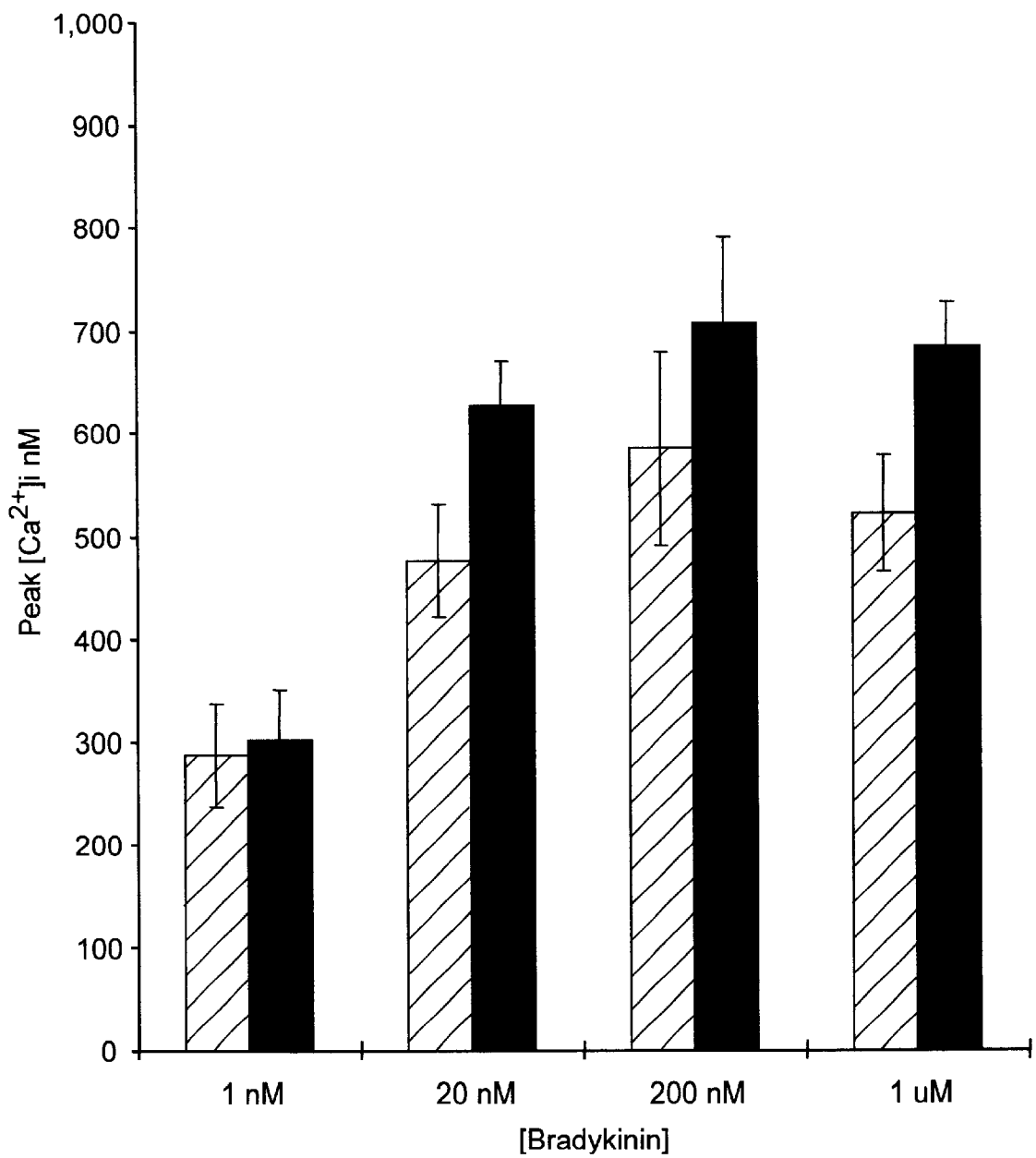

Hours of TNF-α Treatment

DIAGNOSTIC SCREENS FOR TYPE 1 DIABETES (IDDM)

This application claims the benefit of Provisional No. 60/097,518 filed Aug. 20, 1998.

BACKGROUND OF THE INVENTION

Approximately 16 million people (roughly 6% of the population) in the United States suffer from diabetes. Diabetes is the seventh leading cause of death (sixth leading cause of death by disease) in the United States claiming approximately 200,000 lives each year. Moreover, diabetes is one of the most costly health problems in America, running upwards of $92 billion in health care costs annually. Life-threatening complications associated with diabetes include cardiovascular disease and stroke, high blood pressure, blindness, kidney disease, nerve disease and amputation. Of the 16 million diabetics in the United States, approximately 5–10% suffer from IDDM (Insulin-Dependent Diabetes Mellitus) otherwise known as Type 1 diabetes. At least 30,000 new cases of IDDM are diagnosed each year. Persons with IDDM fail to produce insulin and, accordingly, are required to take daily insulin injections in order to stay alive. Many people are unaware that they have diabetes until they develop one or more of its life-threatening complications. Accordingly, much biomedical research has focussed on the cause and development of diabetes with the hope that having a better understanding of the disease will ultimately aid in earlier detection and/or better therapeutic treatments.

With regards to IDDM or Type 1 diabetes, three major theories have been advanced to account for the pathogenesis of the disease. The first is that IDDM is an inherited, or genetic disease. The second, that IDDM results from autoimmunity. The third theory states that IDDM is brought about by an environmental insult, presumably viral (Cotran (1989) *Robbins Pathologic Basis of Disease* 994–1005; Foster (1991) *Harrison's Principles of Internal Medicine* 1739–1759). Most agree however, that it is a combination of elements of all three theories that eventuates in IDDM, rather than each of the three acting independently in different individuals.

There is much evidence to support the theory that IDDM is an inherited disease. IDDM tends to aggregate in families, meaning that if one individual in a given family has the disease, each other member of the family has a greater chance of developing it. Certain HLA types, notably those of the D region of chromosome 6, carry an increased risk of IDDM (Cox et al. (1994) *Diabetologia* 37:500–503). Despite the presence of this genetic evidence, the facts remain that IDDM has a low prevalence of direct vertical transmission, and that the concordance rate of IDDM in monozygotic twins is only 20% (Cotran supra; Foster supra). This indicates that something more complex than simple Mendelian genetics is operating to cause the disease.

Several features of the pathogenesis of IDDM, resemble those of autoimmune diseases. Notably, patients newly diagnosed with IDDM have infiltration of the islets with activated T lymphocytes and antibodies directed against islet cell antigens, which are also present in the serum of non-diabetic siblings destined to develop the disease (Foster supra).

The third theory of the development of IDDM holds that diabetes results from environmental insult. Certain toxins can result in destruction of the pancreas, but the more likely offending agent is a virus. Infection with coxsackie B virus, congenital rubella, measles, mumps, cytomegalovirus, hepatitis, and infectious mononucleosis all carry increased risk of subsequent development of IDDM (Cotran supra; Foster supra). Pancreatic infection with one of these viral agents could bring about β-cell destruction via direct inflammatory disruption, or by induction of an immune response (Foster supra).

More likely than one or the other of these theories explaining IDDM in a given individual is the combination of the three hypothesized causes participating in a sequence of events which results in the destruction of the β-cell, and overt IDDM (Foster supra). A viral infection in a genetically predisposed individual could bring about an inappropriately large inflammatory response in the pancreas. Local inflammation can bring about the increased expression of novel MHC molecules on the surface of islet cells. In particular, the cytokines TNF-α and IL-1β, important players in the inflammatory response, have been shown to increase MHC expression on pancreatic β-cells (Campbell and Harrison (1989) *J. Cell Biochem.* 40:57–66; Han et al. (1996) *J. Autoimmunol.* 9:331–339; Picarella et al. (1993) *J. Immunol.* 150:4136–4150; Ohashi et al. (1993) *J. Immunol.* 150:5185–5194). Novel MHC expression could bring about the eventual antibody formation and autoimmune destruction of the β-cells, with IDDM as the result.

IDDM results from destruction of the insulin-producing β-cells of the pancreatic islets. Without insulin, glucose is not effectively taken up into such metabolically active tissues as muscle, liver or adipose tissue. The results is hyperglycemia. Fasting blood glucose levels greater than 7.8 mM, or non-fasting levels greater than 11 mM result in the diagnosis of diabetes. Although levels of blood glucose are very high in uncontrolled diabetics, the body senses a "starved" state, and begins to release free fatty acids from adipose tissue. The blood levels of free fatty acids in the early stages of ketoacidosis can be in excess of 2 mM. Fatty acids are used as fuel by the liver and by muscle tissue because they can enter the cell freely, whereas glucose can no longer enter due to lack of insulin. The insulin deficiency, together with elevated free fatty acids stimulates gluconeogenesis, further exacerbating the hyperglycemia. The abundance of fatty acid oxidation occurring in the liver leads to an excess production of acetyle CoA. The excess acetyl CoA is converted into ketone bodies. Elevation and underutilization of ketone bodies and fatty acids produces a metabolic acidosis, termed diabetic ketoacidosis, which can progress to coma and death if not treated with insulin. The hyperglycemia present in IDDM is thought to contribute to the major pathologies associated with the disease, such as those found in the peripheral nerves, retina, kidney, and vasculature.

Although IDDM patients may have grossly elevated serum levels of free fatty acids, much less is known about how this may contribute to diabetic pathology than is known about hyperglycemia-related pathology. Even in non-ketotic states, IDDM patients have dyslipidemia, or elevated levels of fatty acid in the serum (Azad et al. (1994) *Arch. Dis. Childhood* 71:108–113). Following insulin-induced hypoglycemia, stimulation of diabetics with epinephrine results in increased free fatty acids greater than in controls subjected to the same maneuver (Bolinder et al. (1996) *Diabetologia* 39:845–853; Cohen et al. (1996) *Am. J. Physiol.* 271 :E284–293). Certain fatty acids have effects on various cells ranging from modulation of intracellular $Ca^{2+}$ homeostatis (Deeney et al. (1992) *J. Biol. Chem.* 267:19840–19845, to activation of the nuclear transcription factor NF-kB, and modulation of gene expression (Prentki et al. (1997) *Diabetologia* 40 Suppl 2:S32–41; Prentki and Corkey (1996) *Diabetes* 45:273–283). Elevated extracellular free fatty acids result in increased cytosolic long chain CoA, the effects of which include modulating protein kinase C (PKC) activity, intracellular protein trafficking G-protein activity, endoplasmic reticulum (ER) $Ca^{2+}$-ATPase activity, expression of acetyl-CoA carboxylase and peroxisome proliferation (Prentki et al., supra; Prentki and Corkey (1996) supra; and Brun et al. (1996) 45:190–198).

Perhaps the most widely-accepted therapy for treating IDDM involves daily injection of insulin in combination with blood glucose monitoring and eating behavior modification, indirectly reducing undesirable secondary side effects and the risk of life-threatening complications. Moreover, alternative therapies including pancreas and islet transplantation, autoantigen-based therapies (e.g., glutamic acid decarboxylase (GAD) therapy), and β cell-related peptide adjunctive therapies are being developed and tested. However, it is well-recognized that there remains a need for therapies that are more preventive in nature, in particular, therapies aimed at correcting the underlying abnormalities responsible for IDDM. Furthermore, there exists a need for new diagnostic tools aimed at identifying persons having or who are predisposed to the disease. In particular, there exists a need for methods of diagnosing persons at risk for developing IDDM, particularly during the long subclinical latency period associated with IDDM.

SUMMARY OF THE INVENTION

The present invention features novel methods of diagnosing persons or subjects having diabetes or at risk for developing diabetes. In particular, the present invention features methods of diagnosing Insulin-Dependent Diabetes Mellitus ("IDDM"), also known as Type 1 diabetes. The present invention is based, at least in part, on the discovery of a striking difference in $Ca^{2+}$ mobilization of human skin fibroblasts from patients with IDDM. In ten out of ten cultured cell lines from unrelated subjects with IDDM, hyper-responsive $Ca^{2+}$ mobilization was observed as compared to the response in seven out of seven unrelated control cell lines. Accordingly, in one embodiment the present invention features methods for diagnosing IDDM in a person or subject (e.g., a test subject) which include detecting hyper-responsive $Ca^{2+}$ mobilization in a cell sample obtained from the subject. In a preferred embodiment, detecting hyper-responsive $Ca^{2+}$ mobilization in cells obtained from the subject (e.g., the test subject) includes comparing $Ca^{2+}$ mobilization in those cells to $Ca^{2+}$ mobilization in cells derived from a control subject. $Ca^{2+}$ mobilization, according to the present invention is preferably induced by contacting cells with a stimulatory agent (e.g., bradykinin).

Hyper-responsive $Ca^{2+}$ mobilization was observed in cells particularly in response to treatments that are known to affect the expression of genes and proteins.

Exemplary treatments that caused hyper-responsive $Ca^{2+}$ mobilization to become apparent were exposure to the inflammatory cytokines, TNF-α and IL-1β, that are elevated in newly diagnosed diabetics, and fatty acids, which are also elevated in diabetes. Accordingly, the methods of the present invention further feature contacting cells with a potentiating agent in order to facilitate detection of hyper-responsive $Ca^{2+}$ mobilization in cells. In one embodiment, the potentiating agent is an inflammatory cytokine. Preferably, the potentiating agent is TNF-α or IL-1β. In another embodiment, the potentiating agent is a component of the diabetic milieu. Preferably, the potentiating agent is a free fatty acid ("FFA"), for example, oleate or oleic acid. It is also within the scope of the present invention to contact cells with at least two potentiating agents, for example, prior to determining $Ca^{2+}$ mobilization. For example, cells (e.g., cells from a test subject and/or cells from a control subject) can be contacted or treated with an inflammatory cytokine (e.g., TNF-α or IL-1β) and a free fatty acid (e.g., oleic acid). These treatments change the $Ca^{2+}$ signaling pathway which plays a major role in cell growth and transmitting information from the bloodstream to the interior of the cell.

Yet another aspect of the present invention includes methods for identifying (e.g., diagnosing) subjects at risk for developing IDDM (or having IDDM, for example, subjects whose disease is in the preclinical latency period) based on the striking difference in $Ca^{2+}$ mobilization in fibroblasts from these patients (e.g., as compared to control subjects or to other standards). In one embodiment, the invention features identifying a person or subject (e.g., a test subject) at risk of developing IDDM which includes comparing $Ca^{2+}$ mobilization in cells (e.g., a test cell sample) obtained from the subject to, for example, $Ca^{2+}$ mobilization in cells from a control subject. Preferably, the person or subject at risk is identified by detecting a difference in $Ca^{2+}$ mobilization in the test cell sample as compared to the control cell sample. In a preferred embodiment, a difference is detected in peak $Ca^{2+}$ response (e.g., to a stimulatory or inducing agent). In yet another preferred embodiment, a difference is detected in steady state $Ca^{2+}$ following stimulation with an inducing or stimulatory agent. In a more preferred embodiment, cells (e.g., test cells and/or control cells or an aliquot thereof) are contacted with a potentiating agent (e.g., TNF-α or IL-1β), for example, prior to contacting with an inducing agent. In yet another embodiment, a difference is detected in the $Ca^{2+}$ response increment (e.g., the incremental increase in response between cells treated with potentiating agent and untreated cells). Preferred subjects which benefit from the methodology described here are human subjects. The present invention further features kits for the diagnosis of IDDM or Type 1 diabetes.

BRIEF DESCRIPTION OF THE DRAWINGS

FIG. 2 depicts the effect of exposure of cells to TNF-α (10 ng/ml for 24 hours) on bradykinin-induced $Ca^{2+}$ mobilization.

FIG. 3 depicts the effect of exposure of cells to IL-1β (1 ng/ml for 24 hours) on bradykinin-induced $Ca^{2+}$ mobilization.

FIG. 4 is a bar graph depicting the effect of exposure to TNF-α on peak response to bradykinin in control and diabetic human fibroblasts. Each bar represents the mean of 14 to 33 separate determinations. Cross-hatched bars represent cells isolated from control donors. Solid bars represent cells isolated from diabetic donors. Diabetic is significantly different from control (ANOVA p<0.001).

FIG. 9 depicts the effect of EGTA on peak bradykinin response in untreated and TNF-α treated fibroblasts.

FIG. 10 depicts the effect of exposure to TNF-α on thapsigargin mediated emptying of intracellular $Ca^{2+}$ stores.

DETAILED DESCRIPTION OF THE INVENTION

Figure 1:
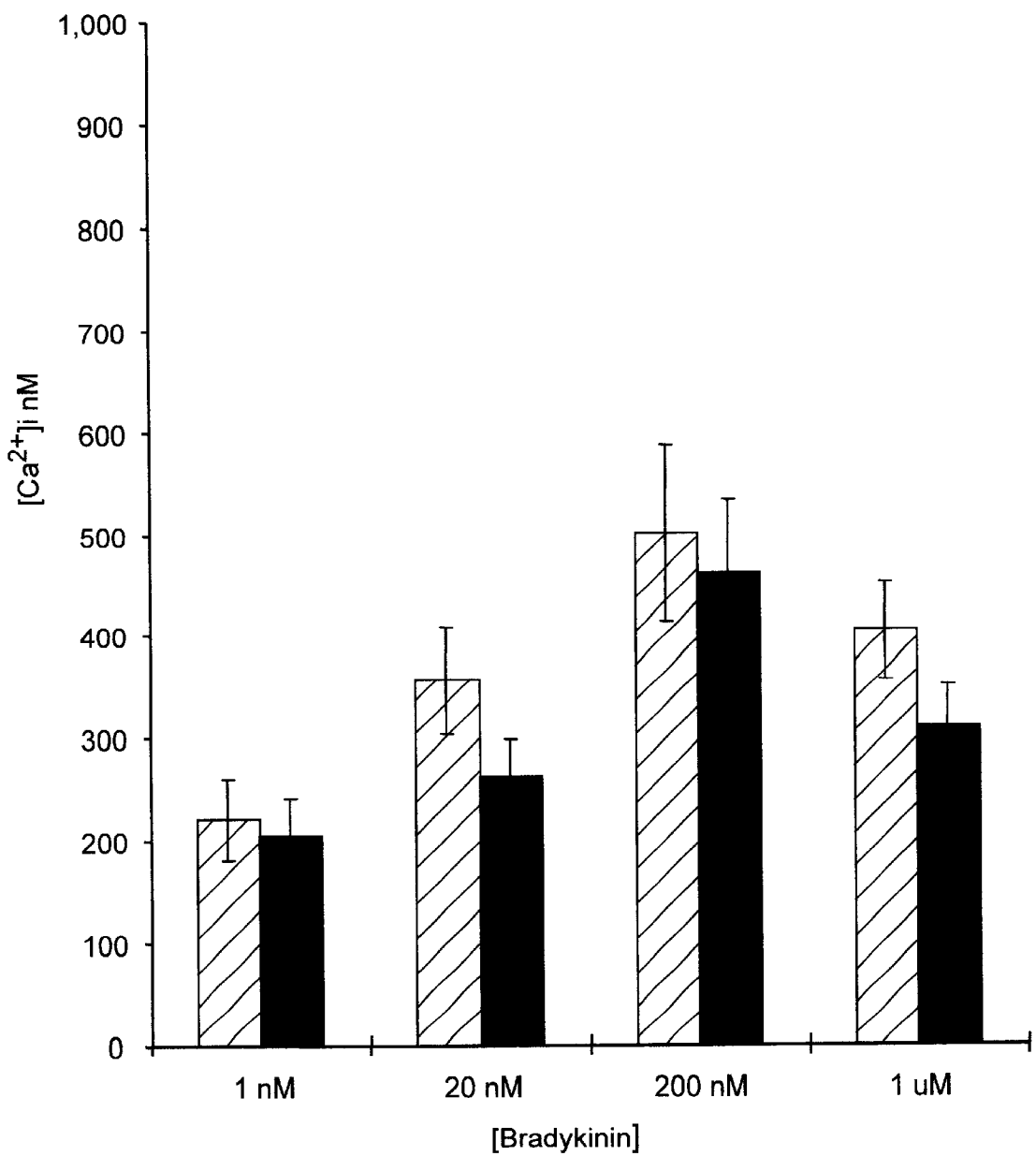
FIG. 1 is a bar graph depicting bradykinin-induced $Ca^{2+}$ mobilization in fibroblasts isolated from control and diabetic human donors. Each bar represents the mean of 14 to 33 separate determinations. Cross-hatched bars represent cells isolated from control donors. Solid bars represent cells isolated from diabetic donors.

Highly significant differences in $Ca^{2+}$ transients between cultured skin fibroblasts from ten unrelated Type 1 diabetic (IDDM) and seven control subjects were observed. The defect in $Ca^{2+}$ signaling, referred to herein as "hyper-responsive $Ca^{2+}$ mobilization", was found in cells from ten of ten patients with IDDM and none of seven controls. There was no overlap between the groups. Non-diabetic siblings exhibited intermediate responses, suggesting a genetic basis for the effect. The three-fold enhancement was observed following exposure for a period of hours to a cytokine such as TNFα or IL-1 β or to free fatty acids (FFA) in the growth media. The changes were prevented by concurrent treatment with cyclohexamide, indicating the involvement of newly synthesized proteins in the defect. Although bradykinin (BK) was used as an agonist to monitor $Ca^{2+}$ transients, the altered responses were not specific to bradykinin since the endoplasmic reticulum (ER) $Ca^{2+}$ stores and the rate and extent of $Ca^{2+}$ uptake were greater in the treated fibroblasts from IDDM subjects than from controls.

Because the defect in $Ca^{2+}$ mobilization (i.e., hyper-responsive $Ca^{2+}$ mobilization) is manifested in a common signal transduction pathway, mobilization of intracellular $Ca^{2+}$, it is possible to identify novel specific genes and/or proteins that are different between controls and diabetics. Identification of these novel genes and/or proteins allows the development of screens to identify susceptible individuals and of appropriate screens for testing potential therapeutic agents. Furthermore, the defect in the $Ca^{2+}$ pathway is predicted to affect responses to many hormones and agonists and because it is a well-understood pathway, provides a good target for testing the effectiveness of putative drugs that might prevent the changes from occurring in susceptible individuals and potentially preventing the development of IDDM. Identification of these novel genes and/or proteins allows the development of appropriate screens for testing potential therapeutic agents.

A. Diagnostic Assays

In one embodiment, the present invention involves a method for diagnosing IDDM in a test subject which includes detecting hyper-responsive $Ca^{2+}$ mobilization in cells obtained from the test subject. The term "hyper-responsive $Ca^{2+}$ mobilization" includes $Ca^{2+}$ responsiveness or $Ca^{2+}$ mobilization in a cells, in particular, mobilization of $Ca^{2+}$ from intracellular stores into the cytoplasm of a cell. $Ca^{2+}$ mobilization can result from contacting a cell, for example, with a stimulatory or inducing agent. The term "stimulatory agent" or "inducing agent" includes any compound or agent that causes a cell (e.g., induces, triggers, stimulates) a cell to mobilize $Ca^{2+}$, for example, from intracellular stores into the cytoplasm of a cell. "Stimulatory agents" or "inducing agents" of the present invention include any agent that acts on a cell through PLC activation. More preferably, inducing agents include any agent that causes release of calcium from the ER of a cell. Exemplary preferred inducing agents include bradykinin, epinephrine, calcium ionophores and the like. Also preferred are, for example, agents that inhibit $Ca^{2+}$-ATPase responsible for sequestering calcium in the ER (e.g., thapsigargin). Cells useful according to the diagnostic methods of the present invention include any cell obtained or isolated form the subject (e.g., test subject or control subject) which is capable of mobilizing calcium. Preferred cells (e.g., test cells and/or control cells include fibroblasts, for example fibroblasts cultured from a skin biopsy, white blood cells, for example peripheral blood leukocytes, fat cells, and the like. Cells can exist in populations as cultures or as single cells (e.g., with $Ca^{2+}$ mobilization detected via an imaging system).

The phrase "detecting hyper-responsive $Ca^{2+}$ mobilization" includes detecting any indicator of the trait defined herein as hyper-responsive $Ca^{2+}$ mobilization. For example, $Ca^{2+}$ mobilization can be determined in a cell according to any methodology familiar to one of ordinary skill in the art and compared to any suitable control or standard to determine that $Ca^{2+}$ mobilization (e.g., $Ca^{2+}$ mobilization in the test cell) is hyper-responsive. $Ca^{2+}$ mobilization can be determined, for example, by loading cells with a calcium-sensitive dye (e.g., a fluorescent or colorimetric calcium-sensitive dye). A preferred calcium-sensitive dye is fura-2 acetoxymethyl ester, also referred to herein as fura-2 AM or fura-2. An exemplary $Ca^{2+}$ mobilization response or $Ca^{2+}$ response includes an increase and peak in intracellular $Ca^{2+}$ concentration followed by a decrease and plateau in intracellular calcium concentration. The initial intracellular $Ca^{2+}$ concentration is referred to herein and in the art as the basal intracellular $Ca^{2+}$ concentration. The ending intracellular $Ca^{2+}$ concentration is referred to as steady state intracellular $Ca^{2+}$ concentration. As described previously, "detecting hyper-responsive $Ca^{2+}$ mobilization" can include determining $Ca^{2+}$ mobilization in a cell according to any methodology familiar to one of ordinary skill in the art and comparing it to any suitable control or standard to determine that $Ca^{2+}$ mobilization is hyper-responsive. In a preferred embodiment, "detecting hyper-responsive $Ca^{2+}$ mobilization" involves comparing $Ca^{2+}$ mobilization in cells obtained from the test subject to $Ca^{2+}$ mobilization in cells obtained from a control subject. Accordingly, the suitable control can be a control cell. The phrase "control cell" includes any cell which exhibits normal traits, as compared to diabetic traits (e.g, hyper-responsive $Ca^{2+}$ mobilization). In one embodiment, control cells are cells of the same cell type as the test cell (or cell obtained or isolated from the test subject) but are obtained or isolated from a control subject (e.g., a subject devoid of IDDM or traits thereof). In another embodiment, control cells are cells obtained or isolated from the test subject but which exhibit normal traits. It is also within the scope of the present invention to use control cells, for example cell lines or cultures, which have predefined characteristics (e.g., have been previously determined to exhibit a normal phenotype). As defined herein, a suitable control can also include a predefined indication of normal phenotype. For example, a normal intracellular $Ca^{2+}$ concentration, for example, for a particular cell type, can be predetermined form analysis of normal cells and that indication used as a control according to the present methodology. In one embodiment, a normal peak intracellular $Ca^{2+}$ concentration can be determined (e.g., following bradykinin stimulation of normal cells) and that number (taking into account reasonable variation) can be used as a suitable control.

The term "detecting hyper-responsive $Ca^{2+}$ mobilization" further includes detecting any protein characteristic of the hyper-responsive $Ca^{2+}$ mobilization trait. For example, the present inventors have demonstrated that hyper-responsive $Ca^{2+}$ mobilization is inhibitable by protein synthesis inhibitors. Accordingly, one of ordinary skill in the art can characterize proteins involved in conferring the hyper-responsive $Ca^{2+}$ mobilization trait on cells and detect the abundance or activity of such proteins as indicating of the hyper-responsive $Ca^{2+}$ mobilization trait.

In another aspect, the method includes the step of contacting the cells with a potentiating agent prior to comparing $Ca^{2+}$ mobilization. Preferred potentiating agent include inflammatory cytokine (e.g., TNF-α, IL-1β, IFN-γ or LIF) as well as certain components of the diabetic milieu (e.g., free fatty acid (FFA), for example, oleic acid). The phrase "diabetic milieu" includes the extracellular environment experienced by a cell, for example, a cell within a diabetic donor. Components of the "diabetic milieu" include any agent that elevates cytosolic free calcium from intracellular stores and preferably can include free fatty acids and/or high glucose. Preferred components of the diabetic milieu include, for example, oleic acid.

Preferred methods of the present invention can further include contacting the cells with two potentiating agents prior to comparing $Ca^{2+}$ mobilization (e.g., TNF-α or IL,-1 β and FFA). The use of a potentiating agent is particularly desirable due to the fact that differences in $Ca^{2+}$ mobilization between normal and control cells are augmented by inclusion of the potentiating agent. For example, peak $Ca^{2+}$ mobilization response in cells from diabetic donors differs from that of control cells (e.g., is enhanced) when both are treated with a potentiating agent. Moreover, steady state $Ca^{2+}$ concentrations in bradykinin-induced cells from diabetic donors differ from that of control cells when both are treated with a potentiating agent. Furthermore, $Ca^{2+}$ mobilization increments (e.g., the incremental increase detected when comparing cells in the presence versus absence of potentiating agent) are detectable only when cells (or at least an aliquot of cells) are treated with potentiating agent. As exemplified herein, potentiation is a time-dependent effect.

Accordingly, when cells are treated with a potentiating agent, they are preferably treated for at least 1 hour, preferably 2 hours, more preferably 3–4 hours, even more preferably between 4 and 12 hours, even more preferably between 12 and 24 hours or greater than 24 hours.

In another embodiment, the present invention involves a method for identifying a subject at risk of developing IDDM or a subject having IDDM which includes obtaining a test cell sample from a test subject, determining $Ca^{2+}$ mobilization in the test cell sample, comparing the $Ca^{2+}$ mobilization in the test cell sample to $Ca^{2+}$ mobilization in a control cell sample from a normal subject, and identifying a subject at risk of developing IDDM or a subject having IDDM by detecting a difference in $Ca^{2+}$ mobilization in the test cell sample as compared to the control cell sample. In a preferred embodiment, the test cell sample and the control cell sample are contacted with a stimulatory agent (e.g., bradykinin) to induce $Ca^{2+}$ mobilization. In another embodiment, the test cell sample and the control cell sample are contacted with a potentiating agent prior to stimulation with the stimulatory agent. A preferred potentiating agent is, for example, an inflammatory cytokine (e.g., TNF-α or IL-1β).

In another embodiment, the present invention involves a method for identifying a subject at risk of developing IDDM or a subject having IDDM which includes obtaining a test cell sample from a test subject, contacting the test cell sample with a stimulatory agent (e.g., bradykinin), determining steady state $Ca^{2+}$ levels in the test cell sample following response of the cell to the stimulatory agent, comparing the steady state $Ca^{2+}$ levels in the test cell sample following response of the cell to the stimulatory agent to steady state $Ca^{2+}$ levels in a control cell sample from a normal subject following response of the control cell to the stimulatory agent, and identifying a subject at risk of developing IDDM or a subject having IDDM by detecting a difference in steady state $Ca^{2+}$ levels in the test cell sample as compared to the control cell sample. In another embodiment, the test cell sample and the control cell sample are contacted with a potentiating agent prior to stimulation with the stimulatory agent. A preferred potentiating agent is, for example, an inflammatory cytokine (e.g., TNF-α or IL-1β).

In yet another embodiment, the present invention involves a method for identifying a subject at risk of developing IDDM or a subject having IDDM which includes obtaining a test cell sample from a test subject, contacting the test cell sample with at least one component of the diabetic millieu (e.g., FFA and/or glucose), determining $Ca^{2+}$ mobilization in the test cell sample, comparing the $Ca^{2+}$ mobilization in the test cell sample to $Ca^{2+}$ mobilization in a control cell sample from a normal subject following response of the control cell to at least one component of the diabetic millieu, and identifying a subject at risk of developing IDDM or a subject having IDDM by detecting a difference in $Ca^{2+}$ mobilization in the test cell sample as compared to the control cell sample. In a preferred embodiment, the test cell sample and the control cell sample are contacted with a stimulatory agent (e.g., bradykinin) to induce $Ca^{2+}$ mobilization. In another embodiment, the test cell sample and the control cell sample are contacted with a potentiating agent prior to stimulation with the stimulatory agent. A preferred potentiating agent is, for example, an inflammatory cytokine (e.g., TNF-α or IL-1β).

In yet another embodiment, the present invention involves a method for identifying a subject at risk of developing IDDM or a subject having IDDM which includes obtaining a test cell sample from a test subject, contacting the test cell sample with at least one component of the diabetic millieu (e.g., FFA and/or glucose), contacting the test cell sample with a stimulatory agent (e.g., bradykinin), determining steady state $Ca^{2+}$ levels in the test cell sample, comparing steady state $Ca^{2+}$ levels in the test cell sample to steady state $Ca^{2+}$ levels in a control cell sample from a normal subject following response of the control cell to at least one component of the diabetic millieu and the stimulatory agent, and identifying a subject at risk of developing IDDM or a subject having IDDM by detecting a difference in steady state $Ca^{2+}$ levels in the test cell sample as compared to the control cell sample. In another embodiment, the test cell sample and the control cell sample are contacted with a potentiating agent prior to stimulation with the stimulatory agent. A preferred potentiating agent is, for example, an inflammatory cytokine (e.g., TNF-α or IL-1β).

Examplary methods of determining mobilization of $Ca^{2+}$ and steady state $Ca^{2+}$ levels in cells are described in detail in the following examples. Furthermore, it is intended that such determinations can be made using alternative methods known in the art for determining mobilization of $Ca^{2+}$ and steady state $Ca^{2+}$ levels in cells.

This invention is further illustrated by the following examples which should not be construed as limiting. The contents of all references cited throughout this application are hereby incorporated by reference.

EXAMPLES

The following examples describe novel findings upon which the present invention is based, at least in part. In particular, the present inventors have determined the effects of tumor necrosis factor alpha (TNF-α) treatment, and the diabetic environment (elevated glucose and fatty acid), on bradykinin-induced $Ca^{2+}$ mobilization in dermal fibroblasts from type 1 diabetic patients and matched controls. Fibroblasts were exposed to TNF-α (10 ng/ml) for up to 48 hours. Cells in suspension were then loaded with fura-2 acetoxymethyl ester, and bradykinin-induced $Ca^{2+}$ mobilization was measured using fluorescence spectrophotometry. Basal intracellular $Ca^{2+}$ levels were significantly lower in diabetic fibroblasts than controls (P<0.05), and TNF-α treatment caused a significant increase in basal $Ca^{2+}$ in diabetic but not control cells (p<0.05). Beginning with 1 hour of TNF-α treatment, increases in $Ca^{2+}$ mobilization in response to bradykinin (1 nM to 1 $\mu$M) were observed in cells from both controls and diabetics. With 24 hours of treatment, TNF-α-induced increments in peak bradykinin response were three-fold greater in diabetics than in controls (P<0.001). Similar results were seen with interleukin-1 beta (IL-1β) treatment. $Ca^{2+}$ transients induced by thapsigargin, an inhibitor of the endoplasmic reticulum $Ca^{2+}$-ATPase, were also greater in TNF-α treated fibroblasts than in untreated cells, with an apparently greater increase in cells from diabetic donors. These data indicate that TNF-α caused an increase in intracellular $Ca^{2+}$ stores, which affected the magnitude of agonist-induced $Ca^{2+}$ responses. Exposing fibroblasts to a combination of 11 mM glucose and 2 mM oleic acid for 48 hours caused increases in both the peak bradykinin response and the TNF-α induced increment in peak response, which were significantly greater in diabetics than controls (p<0.001); 11 mM glucose alone was without effect. That these phenomena were exhibited to a higher degree in cells from type 1 diabetics than in control cells indicates that fibroblasts from diabetic patients have a heightened sensitivity to TNF-α and oleic acid.

Example 1

Cells From Diabetic Donors Exhibit Hyper-Responsive Calcium Mobilization as Compared to Cells From Control Donors As an exemplary agonist of calcium mobilization, bradykinin was first demonstrated to induce calcium mobilization in cells isolated from both control and diabetic donors. Briefly, fibroblasts from 7 control and 10 diabetic donors (passages 7 to 30) were loaded with fura-2 AM and $Ca^{2+}$ mobilization in response to increasing concentrations of bradykinin was determined. As shown in FIG. 1, stimulation of cells from both control and diabetic with 200 nM bradykinin resulted in maximal $Ca^{2+}$ mobilization (peak response), with detectable $Ca^{2+}$ mobilization resulting from 20 nM bradykinin stimulation.

Figure 2A:
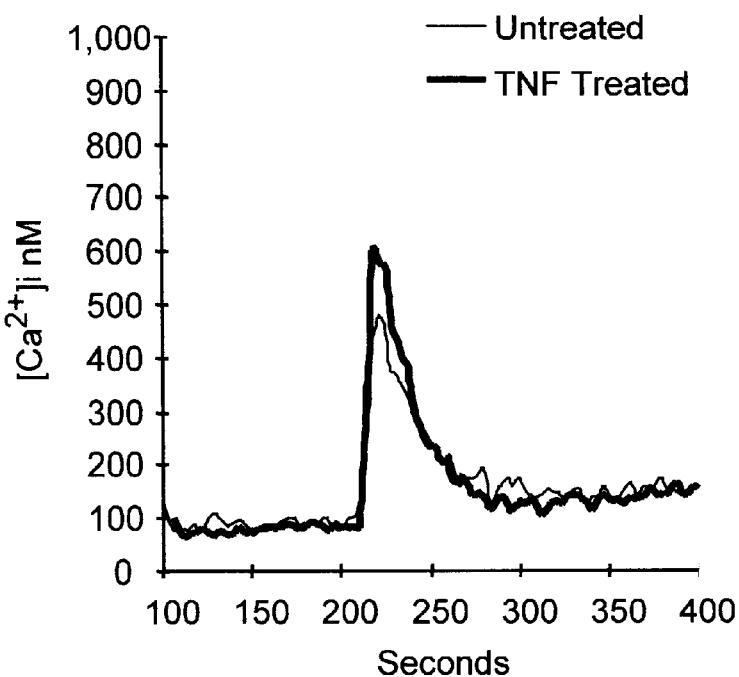
FIG. 2A depicts a trace from a control donor.
Figure 2B:
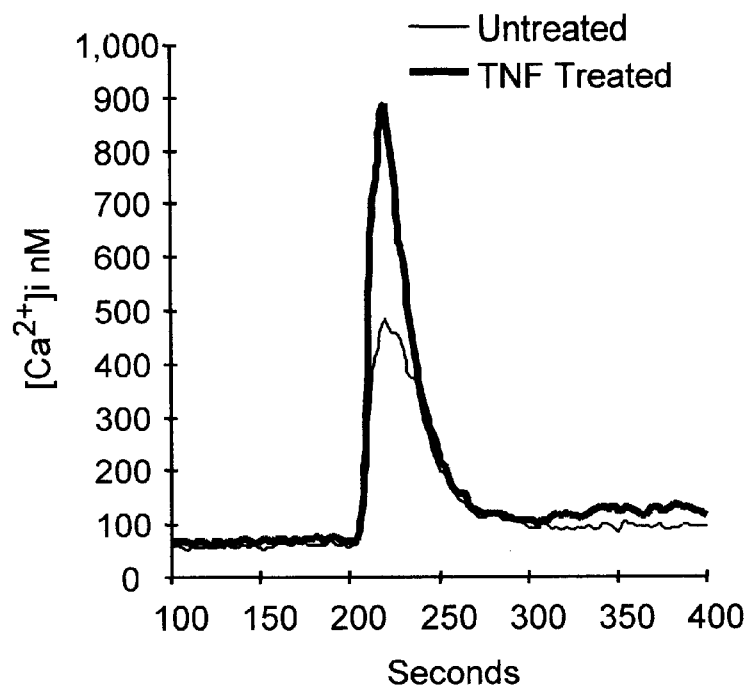
FIG. 2B depicts a trace from a diabetic donor. The traces depicted are representative of traces obtained for all control and diabetic donors.
Figure 3A:
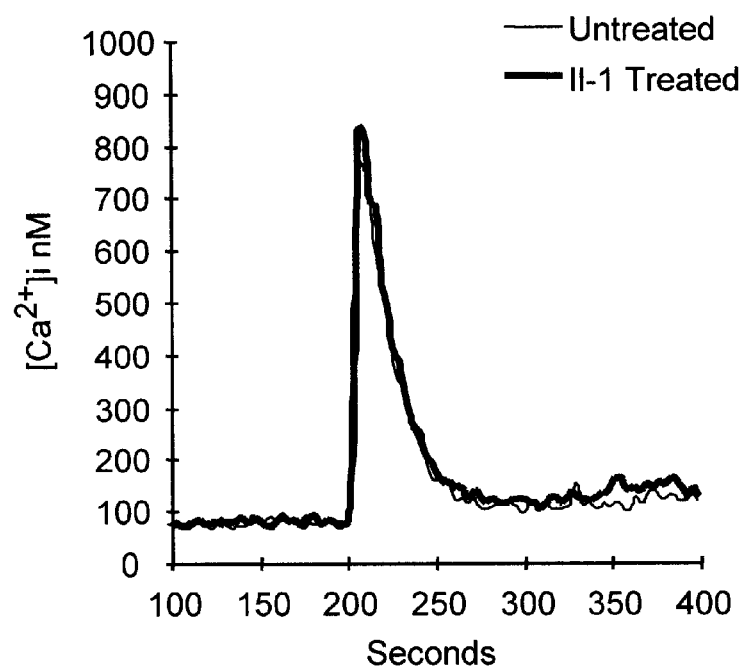
FIG. 3A depicts a trace from a control donor.
Figure 3B:
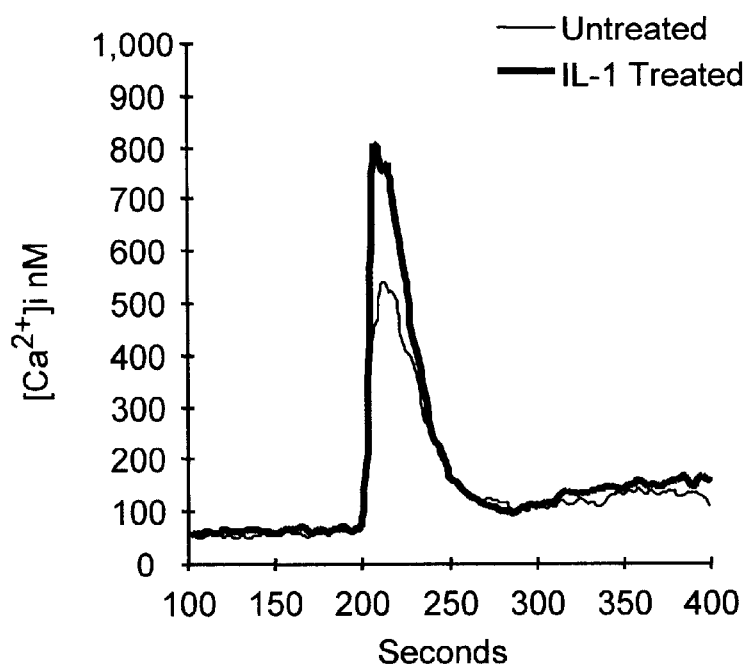
FIG. 3B depicts a trace from a diabetic donor. The traces depicted are representative of traces obtained for all control and diabetic donors.

Inflammatory cytokines such as TNF-α and IL-1β have previously been shown to modulate bradykinin responsiveness in varied experimental systems (O'Neill, Lewis (1989) *Eur. J. Pharmacol.* 166:131–137 and Amrani et al. (1995) *Brit. J. Pharmacol.* 144:4–5). In fibroblasts isolated from control and diabetic donors, a 24 hour incubation with TNF-α (10 ng/ml) potentiated bradykinin-induced $Ca^{2+}$ mobilization, as shown in FIG. 2. Briefly, paired flasks of cells were treated with TNF-α or left untreated. Fura-loaded cells were stimulated with 20 nM bradykinin and $Ca^{2+}$ mobilization was measured after 200 seconds. Similar results were seen with IL-1β treatment (1 ng/ml for 24 hours) (FIG. 3). FIG. 4 shows the effect of TNF-α potentiation (10 ng/ml for 24 hours) on the peak bradykinin-induced $Ca^{2+}$ mobilization response in fibroblasts isolated form 7 control and 10 diabetic (passages 7 to 30) donors. Fibroblasts were fura-2 AM loaded and $Ca^{2+}$ mobilization in response to increasing concentrations of bradykinin was determined. Each bar represents the mean of 14 to 33 separate determinations. In cells from both control and diabetic donors, TNF-α treatment augmented bradykinin induced $Ca^{2+}$ mobilization, although to a much greater extent in the diabetic donor. Statistical analysis of the data indicate that the $Ca^{2+}$ mobilization response in diabetics is significantly different from controls (ANOVA p<0.001). A small increase in the final equilibrium level of $Ca^{2+}$ was also seen consistently in the diabetic fibroblasts, but not in the controls.

The difference between control and diabetic cells can be seen more clearly through the bradykinin-induced increment between untreated and TNF-α treated.

Figure 5:
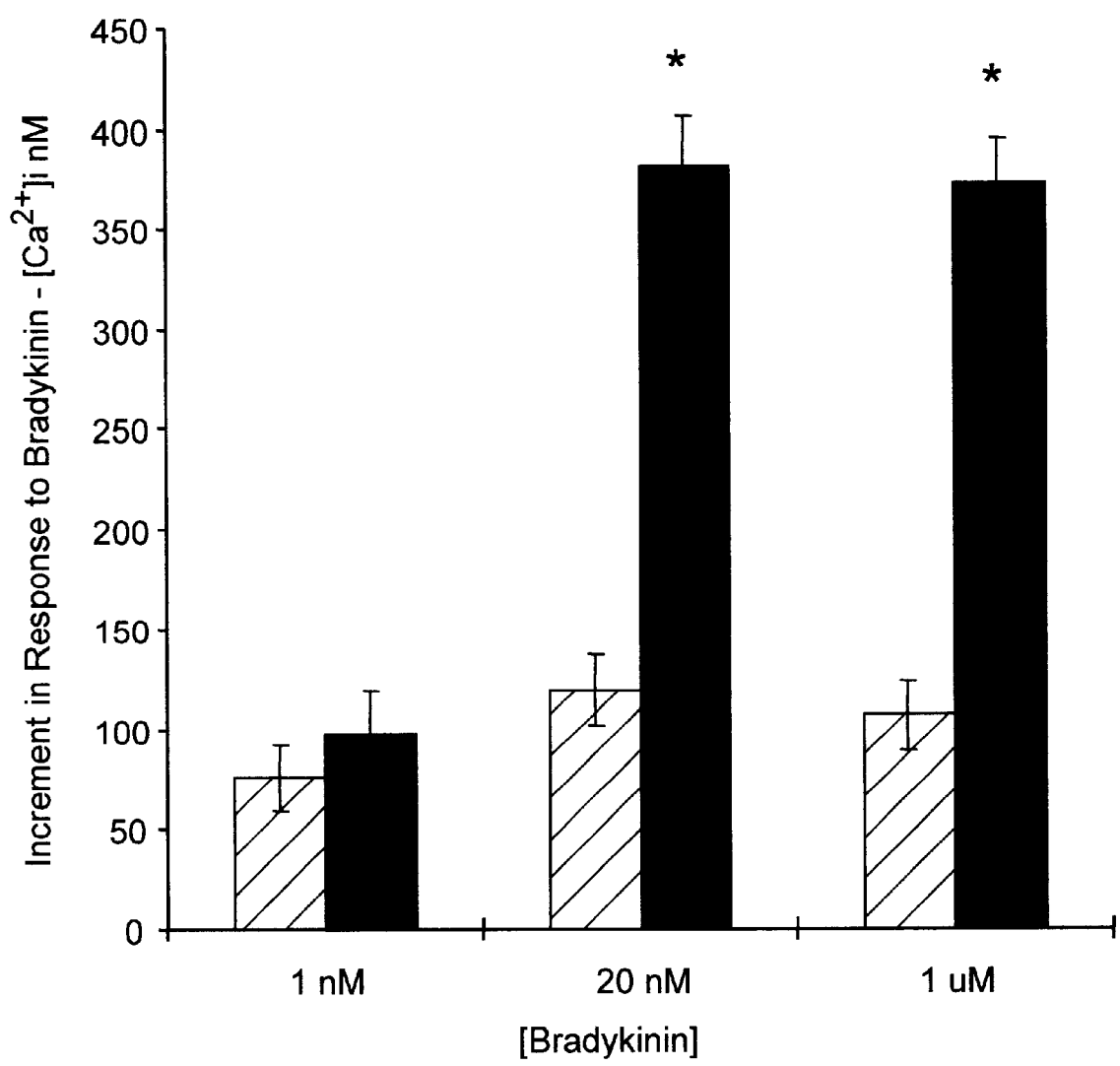
FIG. 5 is a bar graph showing the incremental effect of exposure to TNF-α on bradykinin-induced $Ca^{2+}$ mobilization in human fibroblasts. Each bar represents the mean of 14 to 34 separate determinations. Cross-hatched bars represent cells isolated from control donors. Solid bars represent cells isolated from diabetic donors. * indicates that control is significantly different from diabetic (ANOVA p<0.001).

FIG. 5 shows the incremental effect of exposure to TNF-α (10 ng/ml for 24 hours) on bradykinin-induced $Ca^{2+}$ mobilization in fibroblasts isolated from control versus diabetic humans. The change in peak response to bradykinin after TNF-α treatment was measures in fibroblasts from 7 control and 10 diabetic donors (3–8 separate experiments per donor). Each bar on the graph represents the mean of 14 to 34 separate determinations. When the difference between TNF-α treated and untreated increments was compared, the diabetic cells showed a 3-fold greater effect of bradykinin-induced $Ca^{2+}$ mobilization than control cells. ANOVA indicated an overall difference between control and diabetic (p<0.001), and specific differences between control and diabetic (Tukey p<0.001) at every bradykinin concentration above 1 nM.

Figure 6:
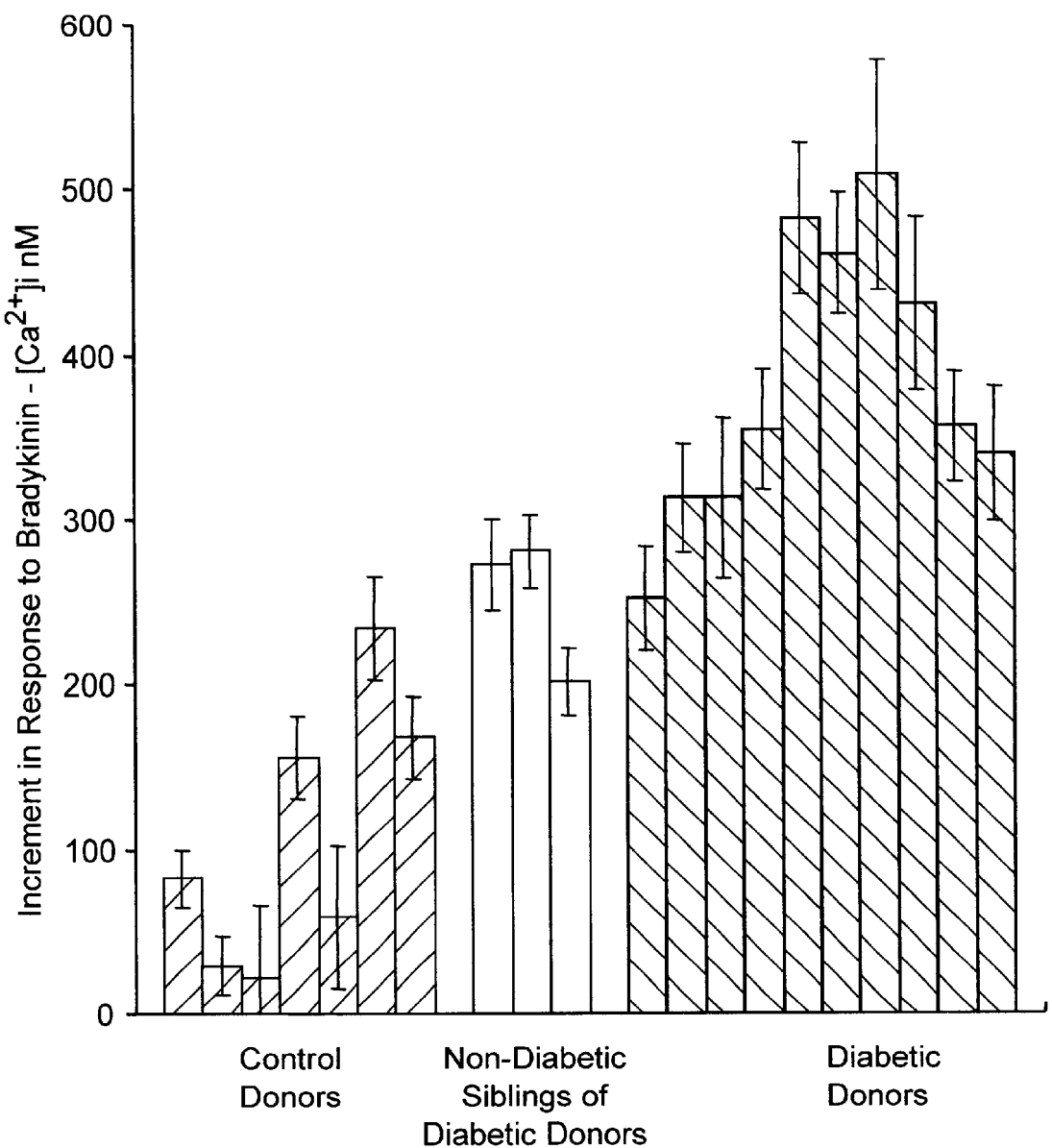
FIG. 6 is a bar graph depicting the incremental effect of exposure to TNF-α on bradykinin-induced mobilization in human fibroblasts in 7 control donors, 3 non-diabetic siblings, and 10 diabetic donors (3–8 separate experiments for each donor). Each bar represents the mean of 6 to 18 separate determinations.
Figure 7:
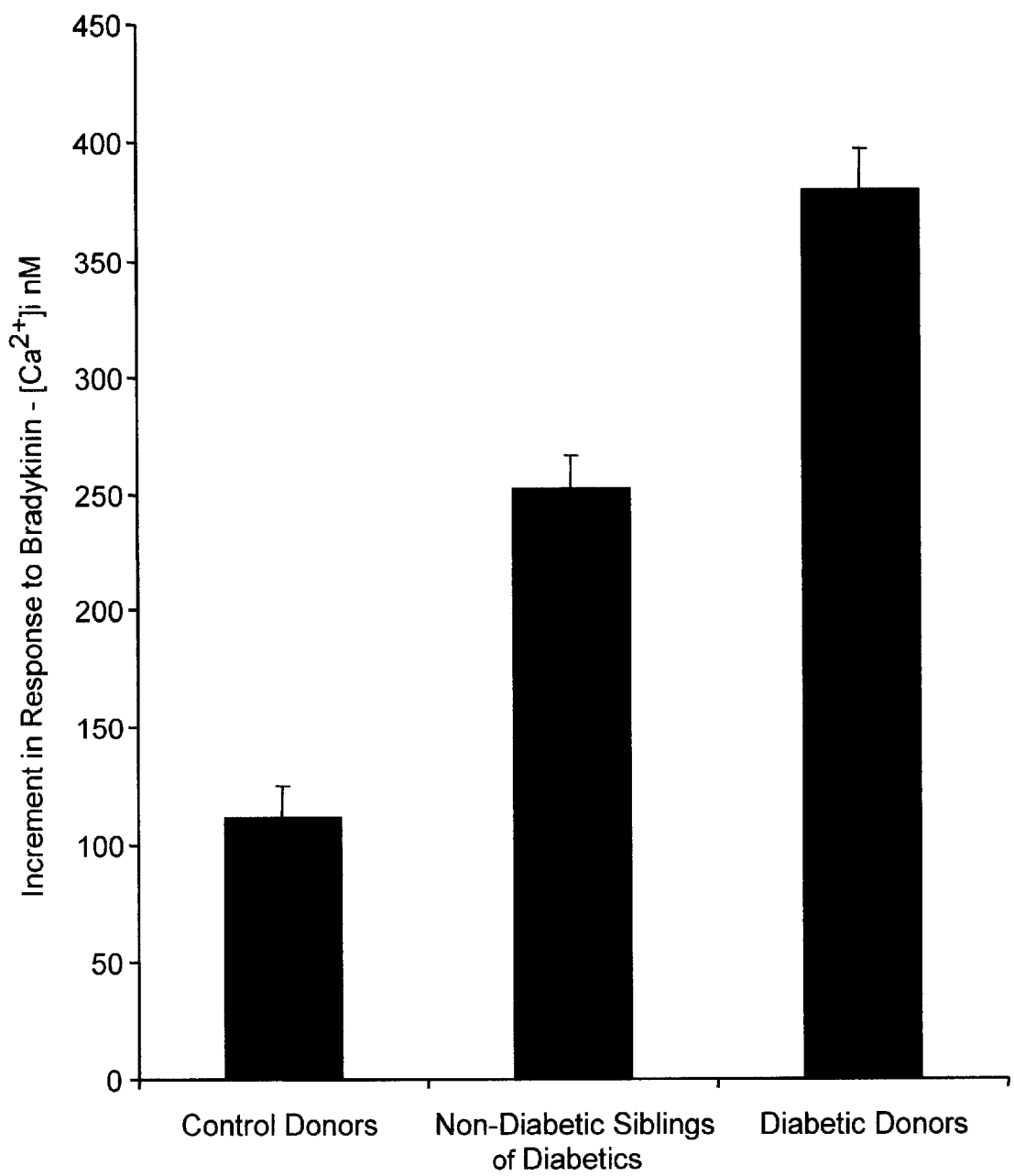
FIG. 7 is a bar graph depicting the average incremental effect of exposure to TNF-α on bradykinin-induced mobilization in human fibroblasts. Each bar represents the mean of 18 to 52 separate determinations. Each groups is significantly different from others (ANOVA p<0.001).

FIG. 6 shows this increment in all of the donors examined. The increment in peak response to bradykinin following TNF-α treatment was determined in 7 control donors, 3 non-diabetic siblings of type 1 diabetics and 10 diabetic donors (3–8 separate experiments per donor). Each bar represents the mean of 6 to 18 separate determinations. The average of these data are shown in FIG. 7. The increments in peak response were pooled (3–8 experiments for each donor). Each bar represents the mean of 18 to 52 separate determinations. Each group is significantly different from the others (ANOVA p<0.001).

Examination of non-diabetic siblings. As the theories of the pathogenesis of IDDM indicated there is some genetic component to the disease, 3 non-diabetic siblings of the 10 previously described diabetic donors (from different families) were obtained to determine whether the non-diabetic siblings more closely resembled their diabetic family members, or their control counterparts in terms of the effects of TNF-α on bradykinin-induced $Ca^{2+}$ mobilization. These subjects are shown in the middle 3 bars of FIG. 6 with average values presented in FIG. 7 of the 7 original control donors, the 10 original diabetic donors and 3 non-diabetic siblings of the diabetics (passages 8 to 15). As can be seen, the non-diabetic siblings of diabetics have a response to TNF-α that is intermediate between the two other groups.

A brief analysis of the TNF-α induced increment in peak bradykinin response in all the donors surveyed showed that the donors can be ranked into 3 different groups, based on the magnitude of their bradykinin response following a TNF-α treatment. Donors with a TNF-α induced increment of less than 200 nM $Ca^{2+}$ can be described as low responders, donors in which the TNF-α induced increment was between 200 and 300 nM $Ca^{2+}$ can be characterized as intermediate responders, and those donors in which the TNF-α induced increment was greater than 300 can be described as high responders. Most the control donors fall into the low responder category, while most of the diabetic donors fall into the high responder category; all of the non-diabetic siblings, and a low percentage of both the controls and the diabetics fall into the intermediate responder category.

This artificial separation into three ordinal groups, according to response to treatment can illuminate possibilities as to the causation of FIDDM, and the lack of a strong concordance rate among siblings for a suspected genetic disease. All of the diabetic donors, and their siblings fall into either the medium or high responders categories, there are no low responders. IDDM comprise a very small percentage of the general population, probably not greater than 1% (Cotran et al. (1989) *Ribbins Pathologic Basis of Disease* 994–1005), and 10 randomly selected fibroblast donors all exhibit greater effects of TNF-α than matched control donors. A trait present in 100% of such a small population must also occur with some frequency in the general population: this explains why some of the control donors approach, or enter the intermediate responder classification. If the causation of diabetes does in fact require a combination of different factors, this can explain why two siblings who both carry a "diabetes gene" can be discordant for the disease. For example, if a genetic predisposition to TNF-α hypersensitivity (which seems to be the case in the diabetic donors, and their siblings studies here, in terms of the TNF-α-induced increment in bradykinin response) mediates autoimmune destruction of pancreatic β cells, then both siblings carrying the hypersensitivity trait would have to encounter the appropriate trigger (e.g., a specific systemic viral infection) to raise TNF-α in the pancreas high enough to mediate insularities. If one sibling contracted a less virulent infection, or avoided the infection all together, insulitis would not occur at that time. A person who does not carry the hypersensitivity trait would not become diabetic by this mechanism, whether or not the appropriate systemic viral injection occurred.

The presence of low, intermediate, and high response groups resembles the effects of autosomal recessive genetic traits. If TNF-α hypersensitivity reflects an autosomal recessive gene, then one would have to be homozygously recessive to be in the high responder group. Homozygous dominant individuals would be low responders, and persons heterozygous for the trait could exhibit incomplete dominance, and be intermediate responders. In this way, a control donor, with no family history of diabetes, could still carry the recessive trait, and be an intermediate responder to TNF-α. Diabetic donors could be intermediate or high responders based on whether they were heterozygous, or homozygous for the trait. If an individual was homozygous recessive, and a hyper-responder to TNF-α, there would be less chance of escaping childhood, and the many viral injections encountered therein, without developing insulities and diabetes. A heterozygous, intermediate responder, however, may encounter the same injections and not develop insulities, because their cells would not respond as vigorously to the same amount of TNF-α.

Example 2

Figure 8:
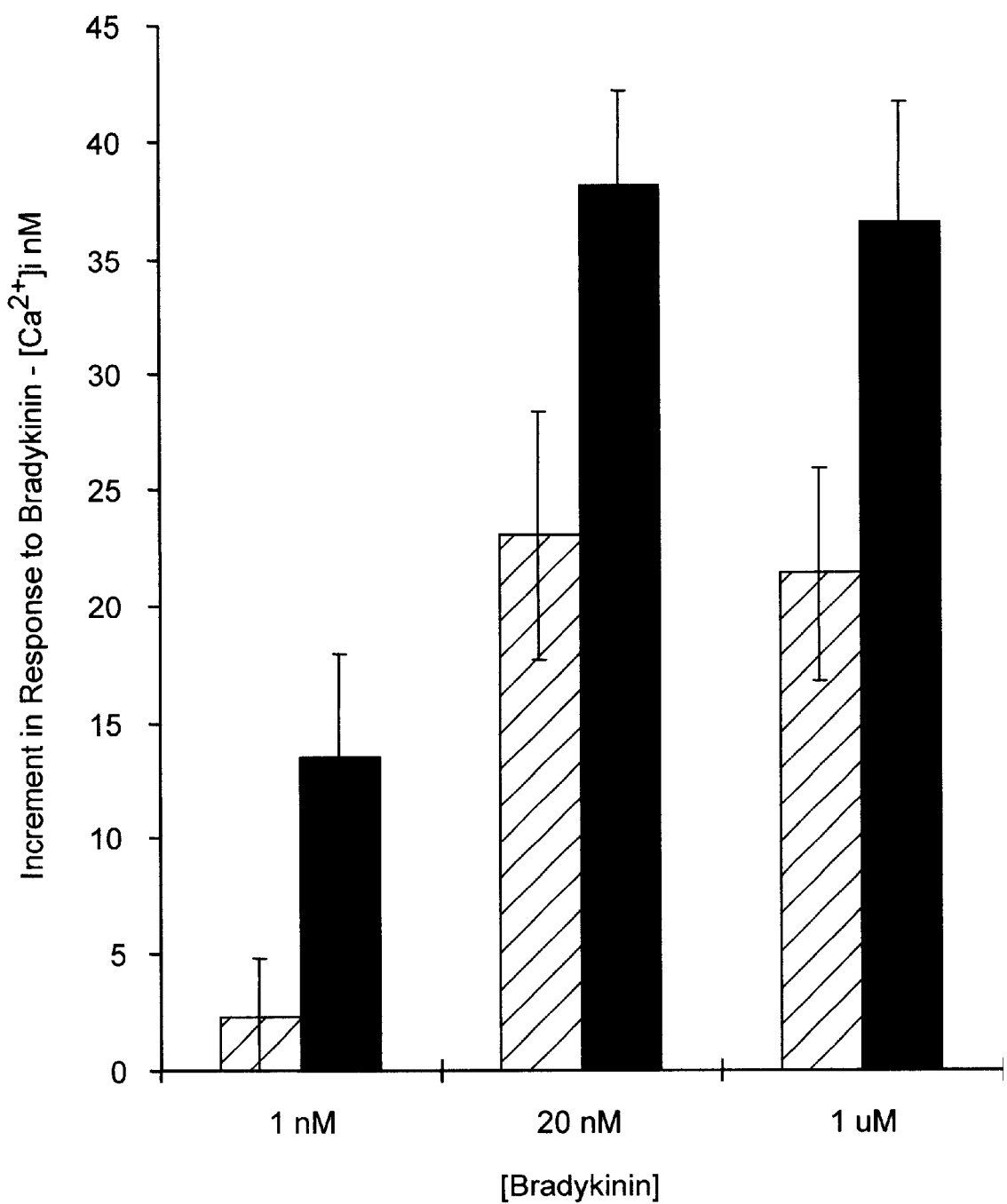
FIG. 8 is a bar graph depicting the incremental effect of exposure to TNF-α on steady state $Ca^{2+}$ following bradykinin stimulation human fibroblasts. The magnitude of the final steady state, or resting intracellular $Ca^{2+}$ following stimulation with bradykinin was determined for 7 control and 10 IDDM donors. Each bar represents the mean of 14 to 34 separate determinations. Cross-hatched bars represent cells isolated from control donors. Solid bars represent cells isolated from diabetic donors. Diabetic cells are significantly different from control at these concentrations of bradykinin (ANOVA p<0.005).

Hyper-Responsive Calcium Mobilization can be Detected as an Increase in Steady State $Ca^{2+}$ in TNF-α-Treated Fibroblasts Following Stimulation with Bradykinin Following the initial bradykinin induced peak of $Ca^{2+}$ mobilized from the ER, a sustained elevation of $Ca^{2+}$ occurs lasting for minutes. This sustained elevation in steady state $Ca^{2+}$ requires $Ca^{2+}$ entry from the extracellular space. Inappropriate elevation of $Ca^{2+}$ may lead to cell injury, apoptosis and death by activation of phospholipases, nucleases, and proteases (Cheung et al. (1986) *N. Engl. J Med.* 314:1670–1676): thus, inappropriately elevated $Ca^{2+}$ in diabetic cells could be an important mechanisms for initiating diabetic pathology. Because of the important signal transducing properties of the sustained phase of the $Ca^{2+}$ response, the effects of TNF-α treatment on the steady state were examined. Briefly, fibroblasts from 7 control and 10 diabetic donors were exposed to 10 ng/ml TNF-α for 24 hours prior to bradykinin stimulation. The magnitude of the final steady state, or resting, intracellular $[Ca^{2+}]$ following stimulation with bradykinin was determined. The incremental effect of exposure to TNF-α was examined and the results are shown in FIG. 8. Each bar represents the mean of 14 to 34 separate determinations. TNF-α treatment caused significant elevations of steady state $Ca^{2+}$ following the bradykinin response in both control and diabetic donors (ANOVA p<0.001) which were significantly higher in the diabetic fibroblasts than in the controls (ANOVA p<0.005).

Example 3

Effect of EGTA on TNF-α-Induced Increases in Peak Bradykinin Response

Figure 9A:
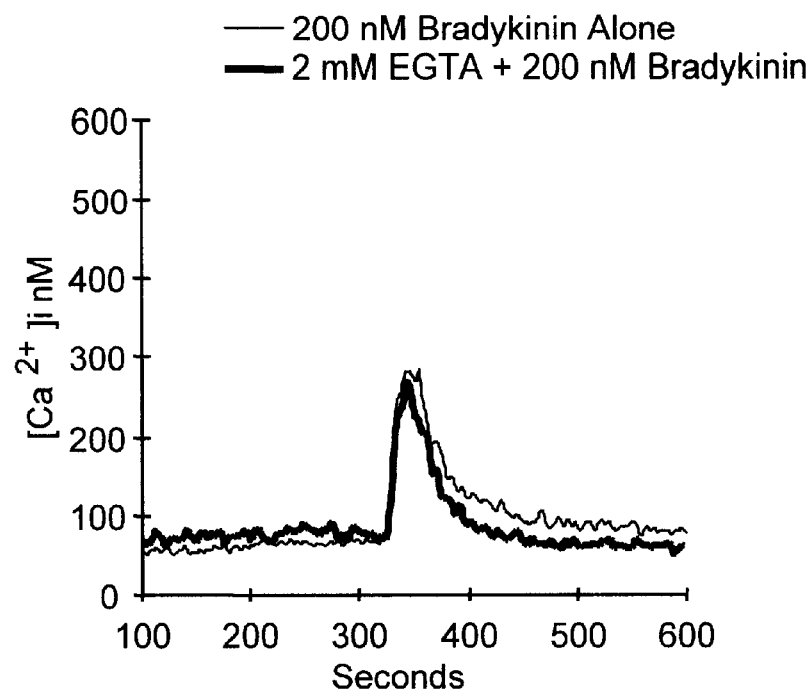
FIG. 9A depicts a trace from an untreated cell population.
Figure 9B:
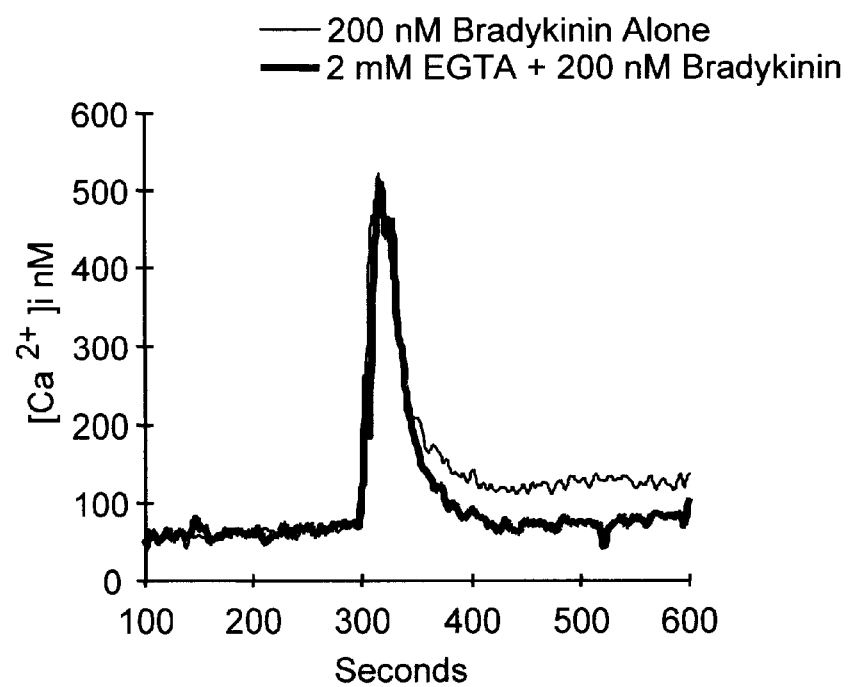
FIG. 9B depicts a trace from a TNF-α treated cell population. These are representative traces from one donor.

To determine whether the TNF-α induced increase in the peak bradykinin response was due to mobilization of $Ca^{2+}$ from intracellular stores, the $Ca^{2+}$ chelator EGTA was added prior to stimulation with bradykinin. FIG. 9 illustrates an experiment in which fibroblasts were treated with TNF-α for 24 hours or left untreated and the peak bradykinin response measured in the presence or absence of 2 mM EGTA. In these traces, 2 mM EGTA was added 10 seconds prior to stimulation with 200 nM bradykinin. The peak response was unaltered by EGTA in untreated and TNF-α treated cells. (EGTA did, however, eliminate the increase in final $[Ca^{2+}]$I). This indicated that extracellular $Ca^{2+}$ did not contribute to the bradykinin induced $Ca^{2+}$ peak, and was not responsible for the TNF-α induced increment in peak response.

Example 4

Effect of TNF-α on Thapsigargin Emptying of Intracellular $Ca^{2+}$ Stores

Figure 10A:
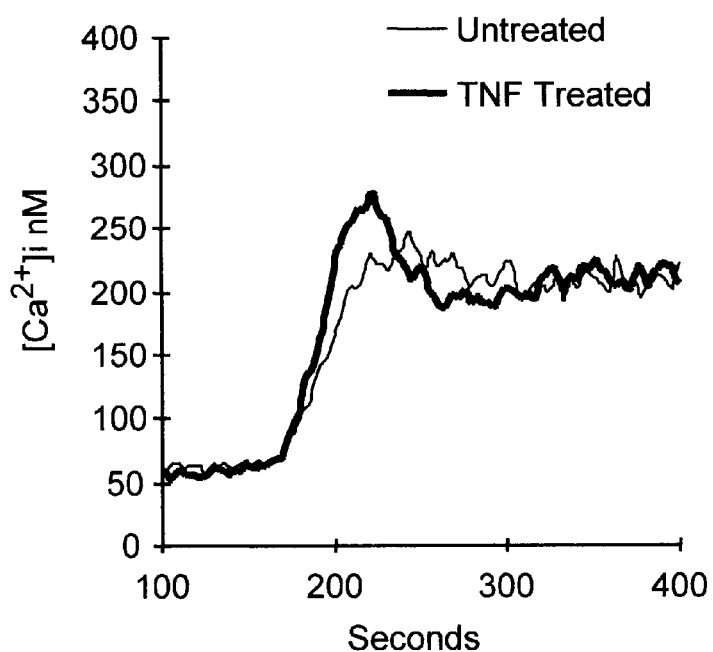
FIG. 10A depicts traces of thapsigargin-treated, fura-loaded fibroblasts from control donors.
Figure 10B:
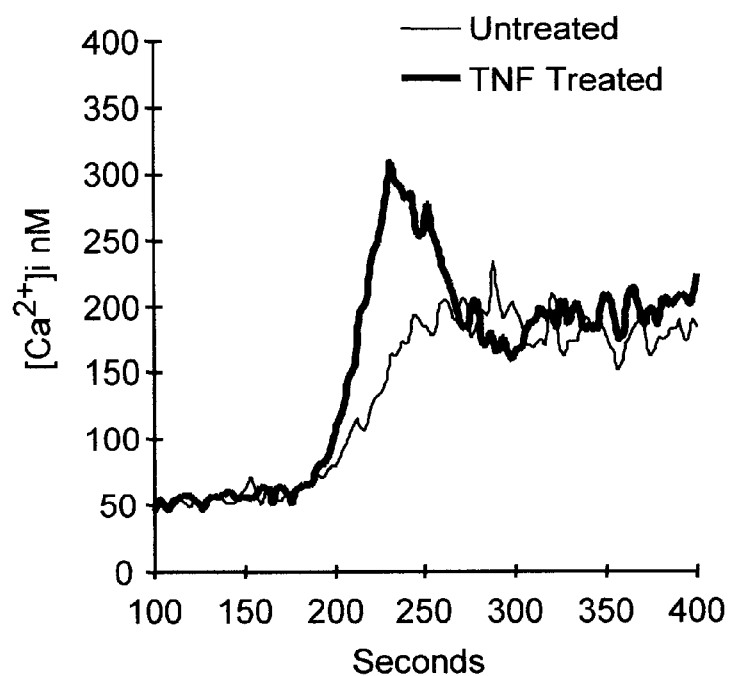
FIG. 10B depicts traces of thapsigargin-treated, fura-loaded fibroblasts from diabetic donors.

Thapsigargin, an irreversible inhibitor of the intracellular $Ca^{2+}$-ATPase, was used to determine if the TNF-α induced increment in peak bradykinin response was mediated by changes in the bradykinin signal transduction cascade, or was at the level of the intracellular $Ca^{2+}$ stores by irreversibly inhibiting their refilling. FIG. 10 illustrates representative traces in which thapsigargin was added to untreated and TNF-α treated cells from control and IDDM donors. Addition of thapsigargin caused $Ca^{2+}$ to leak out of the ER, resulting in a transient rise of cytosolic $Ca^{2+}$, which plateaued at a new set point. In both control and IDDM fibroblasts treated with TNF-α treatment had a greater effect in the diabetic donors than in the controls. Potential mechanisms include alterations in modulation of $Ca^{2+}$-ATPase activity, changes in the ATPase itself or alterations in intraluminal signaling.

Example 5

Figure 11:
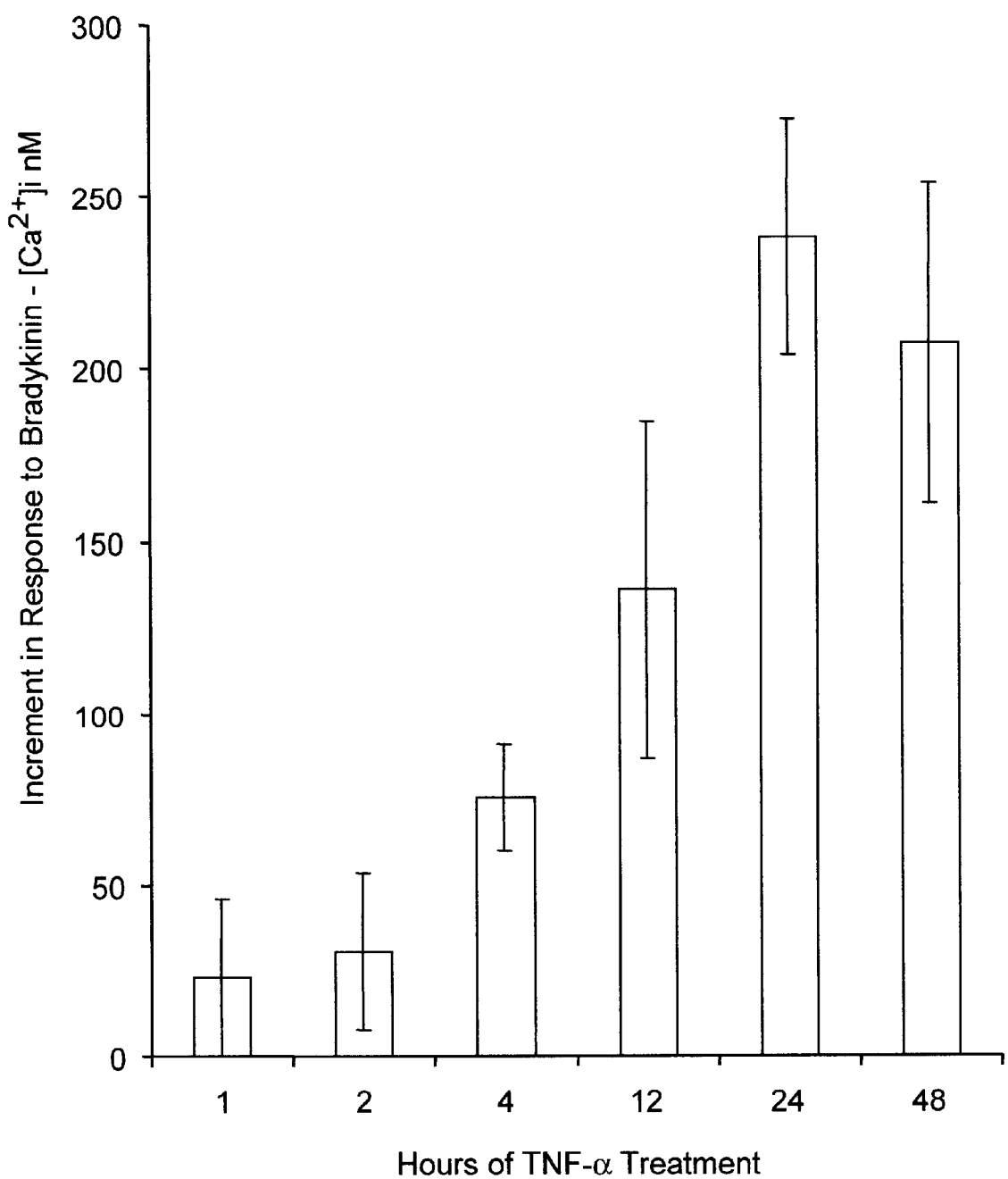
FIG. 11 depicts a time course of the effect of TNF-α pre-treatment on peak bradykinin responses. Fibroblasts from 3 different donors were treated with TNF-α for 1 to 48 hr. After treatment, cells were loaded with fura-2 AM and the TNF-α-induced increment in bradykinin response determined. Each bar represents the mean of 2 to 6 separate determinations.

Time is Required for TNF-α Treatment to Affect Bradykinin-Induced $Ca^{2+}$ Mobilization TNF-α treatments did not have an immediate effect on $Ca^{2+}$ mobilization, but within 24 hours of treatment, a clear and dramatic effect was seen. To determine the time required for TNF-α to induce an effect on peak bradykinin response, a series of time courses were done in 3 different donors (passages 14 to 27), in which fibroblasts were treated with 10 ng/ml TNF-α for 1, 2, 4, 12, 24 or 48 hours. FIG. 11 shows the results of these experiments. Each bar on the graph represents the mean of between 2 and 6 separate determinations. In these donors, a TNF-α induced increment in peak bradykinin response could be seen within a few hours of treatment. A maximum increment was achieved by 24 hour that did not diminished by 48 hr.

Figure 12:
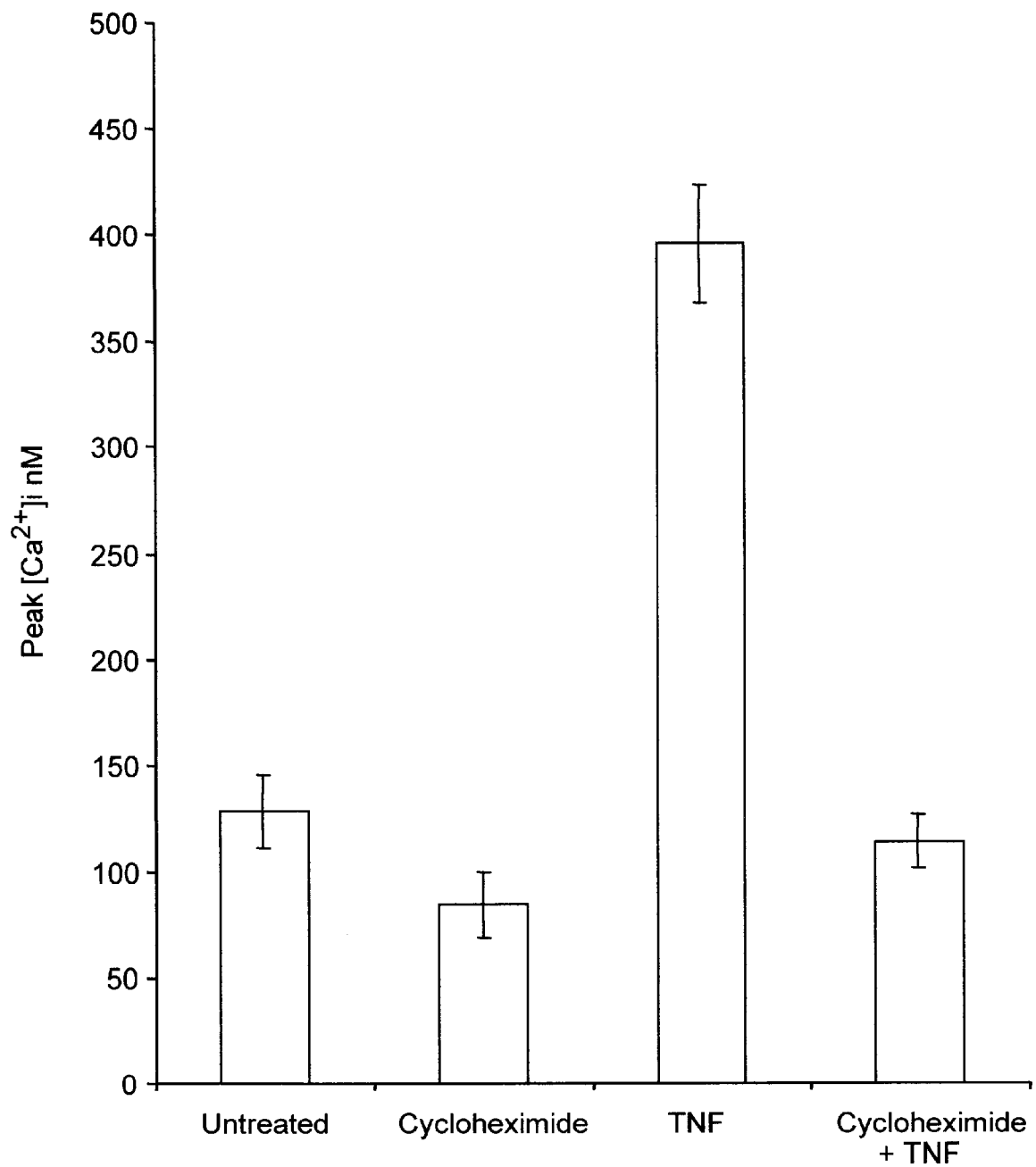
FIG. 12 depicts the effect of cyclohexamide on TNF-α-induced increment in bradykinin response.

These data indicate that time is required for TNF-α to cause an increment in peak bradykinin response, consistent with the possibility of increased protein expression. Consistent with this notion, the protein synthesis inhibitor cycloheximide blocked the TNF-α induced increment (FIG. 12). Changes in calreticulin expression can modulate the responses of $Ca^{2+}$ mobilizing agonists (Liu et al. (1994) *J Biol. Chem.* 269:28635–28639), however, an increase in calreticulin expression did not occur; Western blots shown no change in calreticulin expression did not occur; Western blots shows no change in calreticulin expression after 24 hr of TNF-α treatment or between control and diabetic fibroblasts (data not shown). Although the cycloheximide data indicates that synthesis of new proteins is required for the TNF-α effect, it cannot be concluded from this that TNF-α is responsible for inducing gene expression to achieve that effect. Although TNF-α is known to turn on a multitude of genes in many different cell types, including the fibroblast (Tessier et al. (1993) *Arthritis & Rheumatism* 36:1528–1539; Rathanaswami et al. (1993) *Arthritis & Rheumatism* 36:1295–1304; Butler et al. (1994) *Eur. Cytokine Network* 5:441–448), it is possible that new protein synthesis is required to replete a component of the signal transduction apparatus that is constantly being turned over.

Example 6

Effect of the Diabetic Milieu on TNF-α Induced Peak Bradykinin Responses

Figure 13:
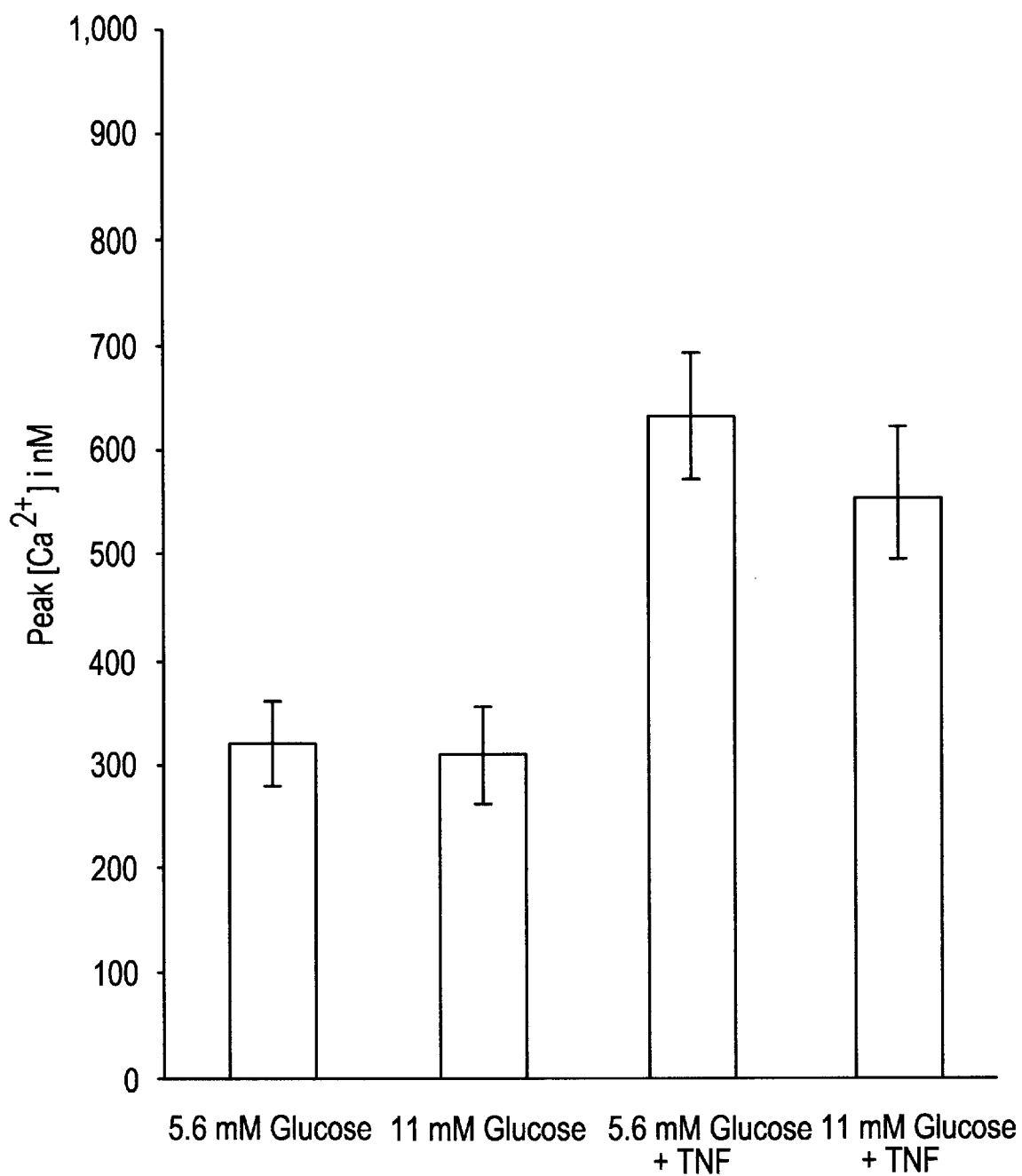
FIG. 13 depicts the effect of glucose and TNF-α on peak bradykinin response in control fibroblasts. 11 mM glucose was added 24 hours before, and throughout the subsequent 24 hour incubation. Each bar on the graph represents the mean of 12 separate determination. TNF-α had a significant effect on bradykinin response (ANOVA p<0.001), but 11 mM glucose did not.

Tight metabolic control of diabetes is recommended to prevent the onset of diabetic pathologies. There is much evidence that suggests that the diabetic environment, specifically, elevated serum glucose levels, is responsible for the generation of these pathologies. The goal of this set of experiments was to assess the effect of a simulated diabetic environment. First, the effects of elevated glucose levels (11 mM) were examined in control and diabetic fibroblasts by comparison to the effect of TNF-α on bradykinin responses in the normal experimental medium (5.6 mM glucose). Fibroblasts were exposed to the experimental medium containing 11 mM glucose for 48 hours. TNF-α treated groups were exposed to TNF-α for the final 24 hours of 48 hour treatment period. Four groups were compared for each donor examined: 5.6 mM glucose alone, 5.6 mM glucose plus TNF-α, 11 mM glucose alone, and 11 mM glucose plus TNF-α. The results of these experiments are shown in FIG. 13. Elevated glucose did not affect controls and diabetics differently, so the results from 3 control donors and 3 diabetic donors (passages 13 to 31) were pooled in this figure. Each bar represents the mean of 12 separate determinations. TNF-α did have its usual significant elevation of peak bradykinin response (p<0.001), but glucose was without further significant effect.

Figure 14:
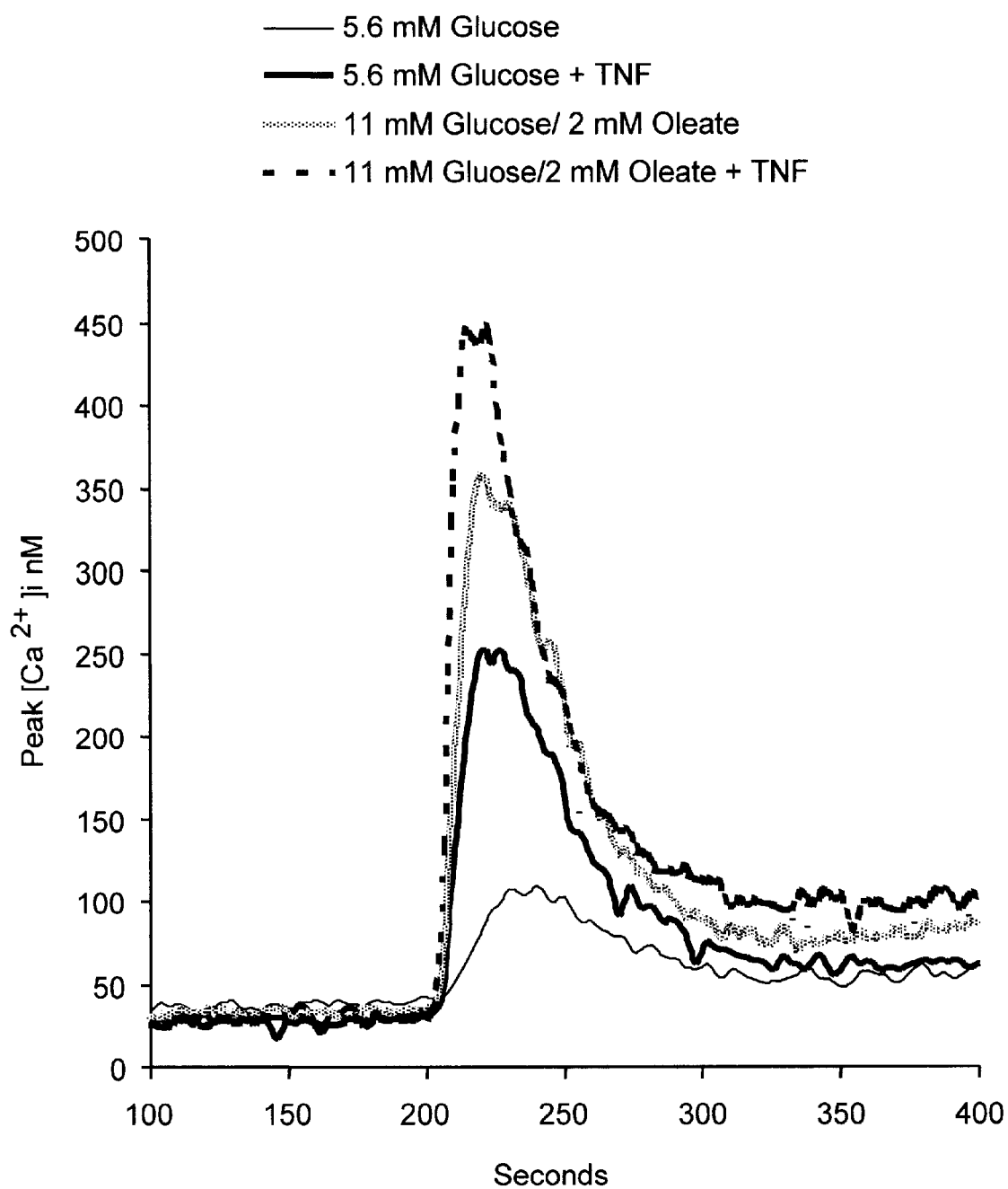
FIG. 14 depicts the effect of glucose, oleate and TNF-α on peak bradykinin response in fibroblasts from an IDDM donor. These are representative traces of bradykinin responses from one diabetic donor. Cells in 5.6 mM glucose were treated for 24 hr with TNF-α (10 ng/ml) or left untreated. Where indicated, 11 mM glucose in combination with 2 mM oleate was added 24 hours before and throughout the subsequent 24 hour incubation. Following 24 hours of incubation, cells were loaded with fura-2 AM and response to 20 nM bradykinin was determined at 200 seconds.
Figure 15:
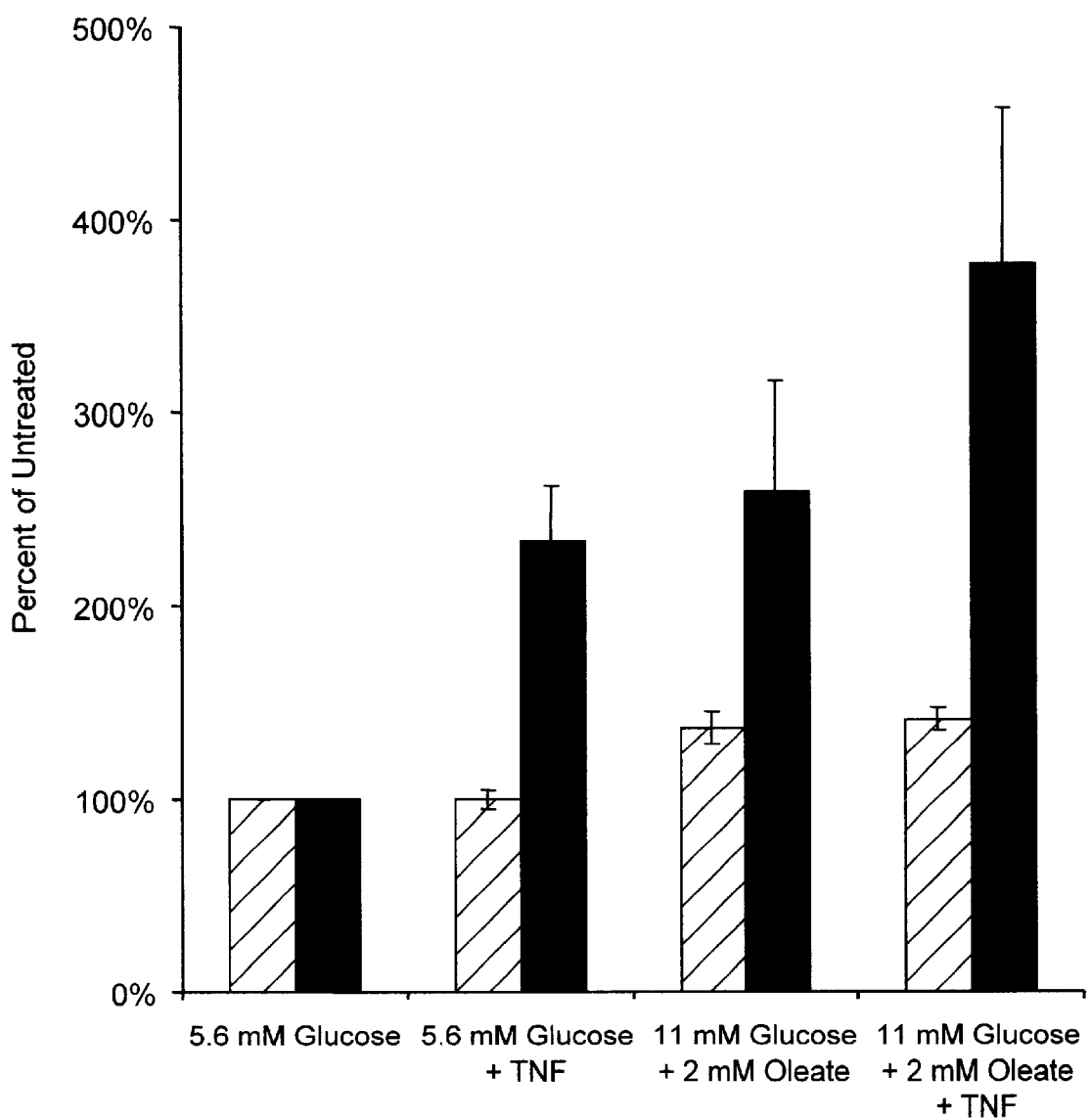
FIG. 15 depicts the effect of glucose, oleate, and TNF-α on peak bradykinin responses in human fibroblasts. Fibroblasts from 3 relatively unresponsive control and 4 diabetic donors were treated for 24 hours with TNF-α (10 ng/ml) or left untreated. Where indicated, 11 mM glucose in combination with 2 mM oleate was added 24 hours before, and throughout the subsequence 24 hour incubation. Following 24 hours of incubation, cells were loaded with fura-2 AM, and peak response to bradykinin was determined, expressed here as a percentage of the untreated condition (5.6 mM glucose). Cross-hatched bars represent cells isolated from control donors. Solid bars represent cells isolated from diabetic donors. Both TNF-α and oleate had significant effects on peak bradykinin response (ANOVA p<0.05 and p<0.001 respectively), and diabetic fibroblasts responded differently from controls (p<0.001).
Figure 16:
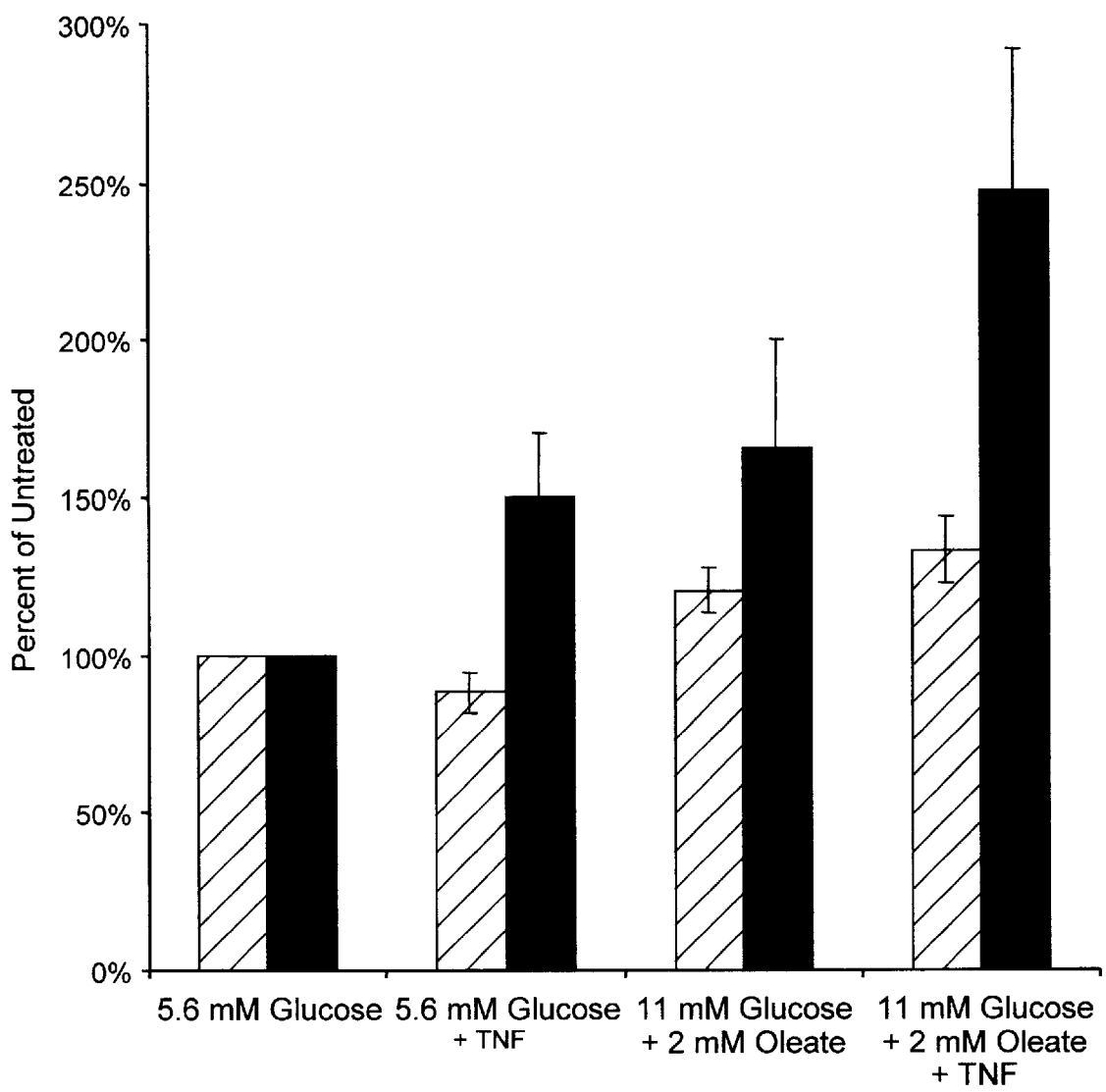
FIG. 16 depicts the effect of glucose, oleate, and TNF-α on steady state $[Ca^{2+}]i$ following bradykinin stimulation in human fibroblasts. Fibroblasts from 3 relatively unresponsive control and 4 diabetic donors were treated with 24 hours of TNF-α (10 ng/ml) or left untreated. Where indicated, 11 mM glucose in combination with 2 mM oleic acid was added 24 hours before, and throughout the subsequent 24 hour incubation. Following 24 hours of incubation, cells were loaded with fura-2 AM, and steady state $[Ca^{2+}]i$ following stimulation with bradykinin was determined, expressed here as a percentage of the untreated condition (5.6 mM glucose). Cross-hatched bars represent cells isolated from control donors. Solid bars represent cells isolated from diabetic donors. Oleic acid had a significant effect on steady state $[Ca^{2+}]i$ (p<0.001), and diabetic fibroblasts responded differently from controls (p<0.001).

Another component of the diabetic milieu is elevated free fatty acid (FFA) in the serum. To examine the effects of FFA on bradykinin induced $Ca^{2+}$ mobilization and on the TNF-α induced increment, fibroblasts from 4 diabetic and 3 control donors (passages 12 to 23) were treated with 2 mM FFA plus 11 mM glucose (from hereon termed FFA medium) for 48 hours. TNF-α treated groups were exposed to TNF-α for the final 24 hours of the 48 hour treatment period. Four groups were compared for each donor examined: 5.6 mM glucose alone, 5.6 mM glucose plus TNF-α. FIG. 14 shows representative traces from an experiment performed on fibroblasts from a single diabetic donor. As can be seen from the superimposed traces (representing the 4 difference treatment conditions), each of the treatments had an effect on both peak bradykinin response, and the sustained phase of the response. Traces from parallel experiments in control donors showed little or no effect of TNF-α and a small effect of the FFA medium, but with less than 25% difference between the lowest (untreated) and highest (FFA medium +TNF-α) peaks (data not shown). The results of the experiments performed in 3 control and 4 diabetic donors were pooled, and are shown in FIG. 15. Each bar on the graph represents the mean of 6 or 8 separate determinations. Peak responses to bradykinin were normalized to a % of 5.6 mM alone.

In experiments to test the effects of the diabetic milieu, the control donors chosen were picked because they had responded to TNF-α treatment with only modest increases in peak bradykinin response in previous experiments and, thus, could exhibit a greater increment in response to treatment. In addition, the 2% BSA used in the media could potentially binding a portion of the TNF-α, possibly explaining the failure of the control fibroblasts to respond vigorously to the TNF-α treatment. Paired T-tests indicated that the effects of the combination of diabetic environment and TNF-α were greater than those of diabetic environment along (p<0.01), and that there was no significant difference between the effects of TNF-α and the diabetic environment. The response of diabetic cells in this medium were significantly greater than control cells. These test media contained both high glucose levels. If control cells had responded like diabetic cells, inferences could have been made to suggestive of a diabetic environment playing a major role in the etiology of IDDM. As high glucose alone did not impact the bradykinin response, the effects of the diabetic medium were most likely due to the presence of FFA.

The major findings in this work can be summarized as follows: 1) fibroblasts from diabetic donors had lower resting $Ca^{2+}$ than fibroblasts from control donors; 2) TNF-α treatment (10 ng/ml for 24 hours) induced an increment in peak bradykinin response (due to increased size of the intracellular stores) and in steady state $Ca^{2+}$ following stimulation with bradykinin, that were significantly greater in diabetic cells than in control cells; 3) the high glucose/high fatty acid environment caused an increment in both peak bradykinin response and steady state $Ca^{2+}$ following stimulation with bradykinin, and diabetics responded differently from controls in this environment. These findings are incorporated into the following model: IDDM fibroblasts have a deficiency in lipid metabolism which leads to the buildup of long chain acyl CoA, which in turn activates the ER $Ca^{2+}$-ATPase, lowering basal $Ca^{2+}$. TNF-α and IL-1β inhibit oxidation of fatty acids (Corkey et al. (1988) *J. Clin. Invest.* 82:782–788; Kilpatrick et al. (1989) *Metabolism* 38:73–77; Nachiappan et al. (1994) *Shock* 1:123–129), leading to a further buildup of cytosolic long chain acyl CoA, further increasing $Ca^{2+}$-ATPase activity, and increasing the size of the bradykinin mobilizable $Ca^{2+}$ stores (Deeney et al. (1992) *J. Biol. Chem.* 267:19840–19845), and bradykinin response by the same mechanism. As diabetic fibroblasts have this preexisting deficiency in lipid metabolism, the effects of TNF-α and oleic acid on bradykinin mobilizable $Ca^{2+}$ stores are exaggerated, as compared to control fibroblasts.

We claim:

1. A method for diagnosing IDDM in a test subject comprising detecting hyper-responsive $Ca^{2+}$ mobilization in cells obtained from the test subject as compared to a suitable control, wherein detection of hyper-responsive $Ca^{2+}$ mobilization correlates with the diagnosis of IDDM.

2. The method of claim 1, wherein detecting hyper-responsive $Ca^{2+}$ mobilization comprises comparing $Ca^{2+}$ mobilization in cells obtained from the test subject to $Ca^{2+}$ mobilization in cells obtained from a control subject.

3. The method of claim 2, wherein comparing $Ca^{2+}$ mobilization comprises contacting the cells with a stimulatory agent to induce $Ca^{2+}$ mobilization.

4. The method of claim 3, wherein the stimulatory agent is bradykinin.

5. The method of claim 2, further comprising contacting the cells with a potentiating agent prior to comparing $Ca^{2+}$ mobilization.

6. The method of claim 5, wherein the potentiating agent is an inflammatory cytokine.

7. The method of claim 6, wherein the potentiating agent in TNF-α.

8. The method of claim 6, wherein the potentiating agent is IL-1β.

9. The method of claim 5, wherein the potentiating agent is a component of the diabetic milieu.

10. The method of claim 9, wherein the potentiating agent is FFA.

11. The method of claim 10, wherein the potentiating agent is oleate.

12. The method of claim 11, comprising contacting the cells with two potentiating agents prior to comparing $Ca^{2+}$ mobilization.

13. A method of identifying a subject at risk of developing IDDM comprising comparing $Ca^{2+}$ mobilization in a test cell sample obtained from the subject to $Ca^{2+}$ mobilization in a control cell sample and identifying the subject at risk by detecting a difference in $Ca^{2+}$ mobilization in the test cell sample as compared to the control cell sample.

14. The method of claim 13, wherein detecting a difference in $Ca^{2+}$ mobilization comprises comparing peak $Ca^{2+}$ response in the test cell sample to peak $Ca^{2+}$ response in the control cell sample.

15. The method of claim 13, wherein detecting a difference in $Ca^{2+}$ mobilization comprises comparing steady state $Ca^{2+}$ in the test cell sample to steady state $Ca^{2+}$ in the control cell sample.

16. The method of claim 13, wherein the test cell sample and the control cell sample are contacted with an inducing agent to induce $Ca^{2+}$ mobilization.

17. The method of claim 13, further comprising contacting the test cell sample with a potentiating agent.

18. The method of claim 13, wherein comparing $Ca^{2+}$ mobilization in the test cell sample to $Ca^{2+}$ mobilization in the control cell sample comprises comparing an incremental increase in $Ca^{2+}$ mobilization in the test cell sample in the presence and absence of potentiating agent to an incremental increase in $Ca^{2+}$ mobilization in the test cell sample in the presence and absence of potentiating agent.

19. The method of claim 1 or 13 wherein the test subject is a human subject.

20. A kit for the diagnosis IDDM in a subject or the risk thereof, comprising a control cell sample, a stimulatory agent, a potentiating agent and instructions for use.

* * * * *